(12) United States Patent
Gaunt et al.

(10) Patent No.: US 9,072,886 B2
(45) Date of Patent: *Jul. 7, 2015

(54) METHOD OF ROUTING ELECTRICAL CURRENT TO BODILY TISSUES VIA IMPLANTED PASSIVE CONDUCTORS

(71) Applicant: Rehabtronics, Inc., Edmonton (CA)

(72) Inventors: Robert Andrew Gaunt, Edmonton (CA); Arthur Prochazka, Edmonton (CA)

(73) Assignee: Rehabtronics, Inc. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/180,972

(22) Filed: Feb. 14, 2014

(65) Prior Publication Data

US 2014/0316497 A1 Oct. 23, 2014

Related U.S. Application Data

(63) Continuation of application No. 13/850,760, filed on Mar. 26, 2013, now abandoned, which is a continuation of application No. 12/400,202, filed on Mar. 9, 2009, now Pat. No. 8,406,886, which is a (Continued)

(51) Int. Cl.
*A61N 1/36* (2006.01)
*A61N 1/05* (2006.01)
(Continued)

(52) U.S. Cl.
CPC .............. *A61N 1/05* (2013.01); *A61B 5/0028* (2013.01); *A61N 1/0504* (2013.01);
(Continued)

(58) Field of Classification Search
CPC ...................... A61N 1/36021; A61N 1/36003

USPC .................. 607/46, 48, 50, 75, 148
See application file for complete search history.

(56) References Cited

U.S. PATENT DOCUMENTS

| 3,204,637 A | 9/1965 | Frank et al. |
| 3,426,748 A | 2/1969 | Bowers |

(Continued)

FOREIGN PATENT DOCUMENTS

| CA | 2484310 | 11/2003 |
| EP | 0862925 | 9/1998 |

(Continued)

OTHER PUBLICATIONS

Supplementary Search Report for European Patent Application No. 08827776.9, mailed Mar. 10, 2011.

(Continued)

*Primary Examiner* — Paula J Stice

(57) ABSTRACT

The invention provides an implant, system and method for electrically stimulating a target tissue to either activate or block neural impulses. The implant provides a conductive pathway for a portion of electrical current flowing between surface electrodes positioned on the skin and transmits that current to the target tissue. The implant has a passive electrical conductor of sufficient length to extend from subcutaneous tissue located below a surface cathodic electrode to the target tissue. The conductor has a pick-up end which forms an electrical termination having a sufficient surface area to allow a sufficient portion of the electrical current to flow through the conductor, in preference to flowing through body tissue between the surface electrodes, such that the target tissue is stimulated to either activate or block neural impulses. The conductor also has a stimulating end which forms an electrical termination for delivering the current to the target body tissue.

39 Claims, 10 Drawing Sheets

Related U.S. Application Data continuation of application No. 11/337,824, filed on Jan. 23, 2006, now Pat. No. 7,502,652, which is a continuation-in-part of application No. PCT/CA2005/000074, filed on Jan. 24, 2005.

(60) Provisional application No. 60/538,618, filed on Jan. 22, 2004.

(51) Int. Cl.
 *A61B 5/00* (2006.01)
 *A61N 1/04* (2006.01)

(52) U.S. Cl.
 CPC ......... *A61N 1/0556* (2013.01); *A61N 1/36021* (2013.01); *A61N 1/36071* (2013.01); *A61N 1/36017* (2013.01); *A61N 1/0472* (2013.01)

(56) References Cited

U.S. PATENT DOCUMENTS

| | | |
|---|---|---|
| 3,774,618 A | 11/1973 | Avery |
| 3,835,864 A | 9/1974 | Rasor et al. |
| 3,964,470 A | 6/1976 | Trombley |
| 3,995,644 A | 12/1976 | Parsons |
| 4,102,344 A | 7/1978 | Conway et al. |
| 4,323,999 A | 4/1982 | Yoshizawa et al. |
| 4,417,888 A | 11/1983 | Cosentino et al. |
| 4,419,995 A | 12/1983 | Hochmair et al. |
| 4,793,353 A | 12/1988 | Borkan |
| 4,922,927 A | 5/1990 | Fine et al. |
| 4,987,897 A | 1/1991 | Funke |
| 5,080,099 A | 1/1992 | Way et al. |
| 5,098,397 A | 3/1992 | Svensson et al. |
| 5,325,870 A | 7/1994 | Kroll et al. |
| 5,330,516 A | 7/1994 | Nathan |
| 5,337,748 A | 8/1994 | McAdams et al. |
| 5,356,428 A | 10/1994 | Way |
| 5,441,518 A | 8/1995 | Adams et al. |
| 5,441,527 A | 8/1995 | Erickson et al. |
| 5,443,065 A | 8/1995 | Berghoff et al. |
| 5,465,715 A | 11/1995 | Lyons |
| RE35,129 E | 12/1995 | Pethica et al. |
| 5,531,782 A | 7/1996 | Kroll et al. |
| 5,545,191 A | 8/1996 | Mann et al. |
| 5,562,707 A | 10/1996 | Prochazka et al. |
| 5,571,148 A | 11/1996 | Loeb et al. |
| 5,578,065 A | 11/1996 | Hattori et al. |
| 5,674,253 A | 10/1997 | Adams et al. |
| 5,702,428 A | 12/1997 | Tippey et al. |
| 5,766,231 A | 6/1998 | Erickson et al. |
| 5,776,178 A | 7/1998 | Pohndorf et al. |
| 5,782,645 A | 7/1998 | Stobie et al. |
| 5,796,827 A | 8/1998 | Coppersmith et al. |
| 5,807,397 A | 9/1998 | Barreras |
| 5,843,132 A | 12/1998 | Ilvento |
| 5,914,701 A | 6/1999 | Gersheneld et al. |
| 5,916,244 A | 6/1999 | Walters |
| 5,948,006 A | 9/1999 | Mann |
| 6,006,122 A | 12/1999 | Smits |
| 6,076,016 A | 6/2000 | Feierbach |
| 6,214,032 B1 | 4/2001 | Loeb et al. |
| 6,233,488 B1 | 5/2001 | Hess |
| 6,259,952 B1 | 7/2001 | Sluijter et al. |
| 6,266,567 B1 | 7/2001 | Ishikawa et al. |
| 6,282,448 B1 | 8/2001 | Katz et al. |
| 6,292,699 B1 | 9/2001 | Simon et al. |
| 6,351,674 B2 | 2/2002 | Silverstone |
| 6,366,814 B1 | 4/2002 | Boveja et al. |
| 6,393,323 B1 | 5/2002 | Sawan et al. |
| 6,415,184 B1 | 7/2002 | Ishikawa et al. |
| 6,438,428 B1 | 8/2002 | Axelgaard et al. |
| 6,505,082 B1 | 1/2003 | Peterfeso et al. |
| 6,564,102 B1 | 5/2003 | Boveja |
| 6,607,500 B2 | 8/2003 | Da Silva et al. |
| 6,629,968 B1 | 10/2003 | Jain et al. |
| 6,635,045 B2 | 10/2003 | Carey et al. |
| 6,668,191 B1 | 12/2003 | Boveja |
| 6,725,096 B2 | 4/2004 | Chinn et al. |
| 6,735,474 B1 | 5/2004 | Loeb et al. |
| 6,735,475 B1 | 5/2004 | Whitehurst et al. |
| 6,754,472 B1 | 6/2004 | Williams et al. |
| 6,788,979 B1 | 9/2004 | Axelgaard et al. |
| 6,829,508 B2 | 12/2004 | Schulman et al. |
| 6,840,919 B1 | 1/2005 | Håkansson |
| 6,847,844 B2 | 1/2005 | Sun et al. |
| 6,879,859 B1 | 4/2005 | Boveja |
| 6,892,098 B2 | 5/2005 | Ayal et al. |
| 6,896,675 B2 | 5/2005 | Leung et al. |
| 6,928,320 B2 | 8/2005 | King |
| 6,941,171 B2 | 9/2005 | Mann et al. |
| 6,961,623 B2 | 11/2005 | Prochazka |
| 6,997,735 B2 | 2/2006 | Ehr et al. |
| 7,004,948 B1 | 2/2006 | Pianca et al. |
| 7,013,179 B2 | 3/2006 | Carter et al. |
| 7,162,303 B2 | 1/2007 | Levin et al. |
| 7,324,853 B2 | 1/2008 | Ayal et al. |
| 7,389,145 B2 | 6/2008 | Kilgore et al. |
| 7,415,309 B2 | 8/2008 | McIntyre |
| 7,502,652 B2 | 3/2009 | Gaunt et al. |
| 7,536,226 B2 | 5/2009 | Williams et al. |
| 8,332,029 B2 | 12/2012 | Glukhovsky et al. |
| 8,406,886 B2 | 3/2013 | Gaunt et al. |
| 8,467,880 B2 | 6/2013 | Glukhovsky et al. |
| 8,483,820 B2 | 7/2013 | Zilberman et al. |
| 8,538,517 B2 | 9/2013 | Glukhovsky et al. |
| 8,738,137 B2 | 5/2014 | Dar et al. |
| 8,862,225 B2 | 10/2014 | Glukhovsky et al. |
| 2001/0002441 A1 | 5/2001 | Boveja |
| 2001/0047167 A1 | 11/2001 | Heggeness |
| 2002/0055779 A1 | 5/2002 | Andrews |
| 2002/0077831 A1 | 6/2002 | Numa |
| 2002/0111663 A1 | 8/2002 | Dahl et al. |
| 2002/0193844 A1 | 12/2002 | Michelson et al. |
| 2003/0028232 A1 | 2/2003 | Camps et al. |
| 2003/0078642 A1 | 4/2003 | Malaney et al. |
| 2003/0139794 A1 | 7/2003 | Jenney et al. |
| 2003/0171792 A1 | 9/2003 | Zarinetchi et al. |
| 2003/0181090 A1 | 9/2003 | Ehr et al. |
| 2003/0199807 A1 | 10/2003 | Dent et al. |
| 2003/0236557 A1 | 12/2003 | Whitehurst et al. |
| 2004/0049235 A1 | 3/2004 | Deno et al. |
| 2004/0130455 A1 | 7/2004 | Prochazka |
| 2004/0176804 A1 | 9/2004 | Palti |
| 2004/0199222 A1 | 10/2004 | Sun et al. |
| 2004/0204686 A1 | 10/2004 | Porter et al. |
| 2004/0220641 A1 | 11/2004 | Wagner et al. |
| 2004/0267333 A1 | 12/2004 | Kronberg |
| 2005/0070970 A1 | 3/2005 | Knudson et al. |
| 2005/0136385 A1 | 6/2005 | Mann et al. |
| 2005/0165461 A1 | 7/2005 | Takeda et al. |
| 2005/0277841 A1 | 12/2005 | Shennib |
| 2006/0027118 A1 | 2/2006 | Tollhupp |
| 2006/0271118 A1 | 11/2006 | Libbus et al. |
| 2007/0060975 A1 | 3/2007 | Mannheimer et al. |
| 2007/0088419 A1 | 4/2007 | Fiorina et al. |
| 2007/0265146 A1 | 11/2007 | Kowalczewski et al. |
| 2008/0004676 A1 | 1/2008 | Osypka et al. |
| 2008/0033510 A1 | 2/2008 | Herregraven et al. |
| 2008/0046053 A1 | 2/2008 | Wagner et al. |
| 2008/0288026 A1 | 11/2008 | Cross et al. |
| 2009/0116926 A1 | 5/2009 | Armour |
| 2009/0116929 A1 | 5/2009 | Shea et al. |
| 2009/0149917 A1 | 6/2009 | Whitehurst et al. |
| 2009/0177131 A1 | 7/2009 | Dar et al. |
| 2009/0326602 A1 | 12/2009 | Glukhovsky et al. |
| 2010/0016929 A1 | 1/2010 | Prochazka |
| 2011/0282412 A1 | 11/2011 | Glukhovsky et al. |

(56) References Cited

U.S. PATENT DOCUMENTS

| | | |
|---|---|---|
| 2013/0138164 A1 | 5/2013 | Dar et al. |
| 2013/0274842 A1 | 10/2013 | Gaunt et al. |

FOREIGN PATENT DOCUMENTS

| | | |
|---|---|---|
| JP | 62-286471 | 12/1987 |
| JP | 07-308392 | 11/1995 |
| JP | 09-276418 | 10/1997 |
| JP | 10-509901 | 9/1998 |
| JP | 2003-501207 | 1/2003 |
| JP | 2005-237941 | 9/2005 |
| WO | WO 95/10323 | 4/1995 |
| WO | WO 00/57950 | 10/2000 |
| WO | WO 01/03768 | 1/2001 |
| WO | WO 04/52450 | 6/2004 |
| WO | WO 05/07120 | 1/2005 |
| WO | WO 05/11541 | 2/2005 |
| WO | WO 05/37367 | 4/2005 |
| WO | WO 05/70494 | 8/2005 |
| WO | WO 06/101917 | 9/2006 |
| WO | WO 06/113654 | 10/2006 |
| WO | WO 06/113801 | 10/2006 |
| WO | WO 07/02741 | 1/2007 |
| WO | WO 07/08906 | 1/2007 |
| WO | WO 07/82382 | 7/2007 |
| WO | WO 08/140242 | 11/2008 |
| WO | WO 09/58258 | 5/2009 |
| WO | WO 11/068849 | 6/2011 |
| WO | WO 2011/068849 | 6/2011 |

OTHER PUBLICATIONS

Office Action for U.S. Appl. No. 12/197,849, mailed Sep. 23, 2011.
International Search Report and Written Opinion for International Application No. PCT/US10/58525, mailed Feb. 7, 2011.
Response to Examination Report for Australian Patent Application No. 2006261666, dated May 11, 2011.
Office Action for Canadian Application No. 2,608,397, dated Jan. 25, 2013.
Office Action for U.S. Appl. No. 11/993,393, mailed Nov. 2, 2011.
International Search Report for International Application No. PCT/US2006/025146, mailed Dec. 12, 2006.
Office Action for U.S. Appl. No. 12/147,937, mailed Feb. 2, 2012.
Office Action for U.S. Appl. No. 12/147,937, mailed Oct. 15, 2012.
Office Action for U.S. Appl. No. 12/147,937, mailed Apr. 25, 2013, 7 Pages.
Office Action for Australian Application No. 2009262237, dated Aug. 12, 2013.
Office Action for Japanese Application No. 2011-516572, mailed Jun. 21, 2013.
Office Action for Japanese Application No. 2011-516572, mailed Jan. 28, 2014.
Office Action for U.S. Appl. No. 13/000,840, mailed Oct. 9, 2012.
Office Action for U.S. Appl. No. 13/000,840, mailed Nov. 8, 2013.
Office Action for U.S. Appl. No. 13/000,840, mailed Oct. 8, 2014.
International Search Report and Written Opinion for International Application No. PCT/US2009/048419, mailed Aug. 18, 2009.
International Search Report for International Application No. PCT/CA2005/000074, mailed Jun. 21, 2005.
International Search Report and Written Opinion for related International Application No. PCT/CA2007/000077, mailed May 15, 2007.
Office Action for European Patent Application EP 05700290.9, mailed Jun. 16, 2009.
Office Action for European Patent Application EP 05700290.9, mailed Jan. 27, 2009.
Partial Translation of Office Action for Japanese Patent Application No. JP 2004-543869, dated May 26, 2009.
Supplementary European Search Report for European Patent. Application EP 05700290.9, mailed Jan. 27, 2009.
Supplementary European Search Report for European Patent Application EP 07701705.1, mailed Jun. 7, 2010.
International Search Report and Written Opinion for International Application No. PCT/CA2010/001487, mailed Jan. 18, 2011.
Abel-Gawad, M. et. al., "Reduction of bladder outlet resistance by selective stimulation of the ventral sacral root using high frequency blockage: a chronic study in spinal cord transected dogs," Journal of Urology, vol. 166 (2001), pp. 728-733.
Ade-Hall, R. et al., "Botulinum toxin type a in the treatment of lower limb spasticity in cerebral palsy (Review)," the Cochrane Library (2009), Issue 3, 19 Pages.
Amis, a. et al., "Relative Displacements in Muscle and Tendon During Human Arm Movements," J. Physiol. (1987), vol. 389, pp. 37-44.
Apkarian, J. A. et al., "Stretch reflex inhibition using electrical stimulation in normal subjects and subjects with spasticity," Journal of Biomedical Engineering, vol. 13 (1991), pp. 67-73.
Ashkan, K. et al., "Deep brain stimulation of the subthalamic nucleus in Parkinson's disease 1993-2003: where are we 10 years on?," Br J. Neurosurg, vol. 18 (2004), pp. 19-34.
Benabid, a. L. et al., "Combined (Thalamotomy and stimulation) stereotactic surgery of the VIM thalamic nucleus for bilateral Parkinson disease," Applied Neurophysiology, vol. 50 (1987), pp. 344-346.
Bhadra, N. et al., "High-frequency electrical conduction block of mammalian peripheral motor nerve," Muscle & Nerve (EPUB ahead of Dec. 2005 print) (2005), pp. 782-790.
Bhadra, N. et al., "Direct Current Electrical Conduction Block of Peripheral Nerve. IEEE Transactions on Neural Systems and Rehabilitation Engineering," vol. 12, No. 3 (Sep. 2004), pp. 313-324.
Brindley, G. S. et al., "Sacral anterior root stimulators for bladder control in paraplegia," Paraplegia, vol. 20 (1982), pp. 365-381.
Broseta, J. et al., "High-frequency cervical spinal cord stimulation in spasticity and motor disorders," Acta Neurochir Suppl (Wien), vol. 39 (1987), pp. 106-111.
Cattell, M. et al., "The ' Inhibitory' Effect of High—Frequency Stimulation and the Excitation State of Nerve," Department of Physiology, University College, London (Nov. 1934), pp. 407-415.
Filali, M. et al., "Stimulation—induced inhibition of neuronal firing in human subthalamic nucleus," Exp Brain Res, vol. 156(3) (2004), pp. 274-281.
Gans, L. et al., "The Stimulus Router: A Novel Means of Directing Current From Surface Electrodes to Nerves," 10th Annual Conference of the International FES Society (Jul. 2005), Montreal, Canada, pp. 2123.
Gans et al., "The Stimulus Router: A Novel Means of Directing Current From Surface Electrodes to Nerves," 10th Annual Conference of the International FES Society (Jul. 2005), Montreal, Canada, Display Poster.
Glenn, W. W. et al., "Radiofrequency—controlled catheter pacemaker, Clinical application," New England Journal of Medicine, vol. 275 (1966), pp. 137-140.
Grill, W. M., Jr. et al., "Quantification of recruitment properties of multiple contact cuff electrodes," IEEE Trans. Rehabil. Eng., vol. 4(2) (1996), pp. 49-62.
Groen, J. et al., "Neuromodulation techniques in the treatment of the overactive bladder," BJU Int, vol. 87(8) (2001), pp. 723-731.
Handa, Y. et al., "Application of functional electrical stimulation to the paralyzed extremities," Neurologia Medico—Chirurgica, vol. 38 (1998), pp. 784-788.
Haugland, M. et al., "Interfacing the body's own sensing receptors into neural prosthesis devices," Technology Health Care, vol. 7 (1999), pp. 393-399.
"Innovative Medical Devices for Neuro-Technologies," NeuroTECH, [online] [Retrieved on Sep. 21, 2007] Retrieved from the Internet: <URL: http://www.neurotech.be/Prodcuffelectrode.htm>.
Jankovic, J. et al., "Outcome after Stereotactic Thalamotomy for Parkinsonian, Essential, and Other Types of Tremor," Neurosurgery Online [online] [retrieved on May 21, 2009] Retrieved from the Internet: <URL:http://www.ovidsp.tx.ovid.com/spa/ovidweb.cgi?&S=AACMFPFHBADDKOHCNCFLGDMJJ...I> 9 Pages.
Kilgore, K. L. et al., "Chapter 6.2: Upper and lower extremity motor neuroprostheses," Horch, K.W. And Dhillon, G.S., ed., Neuroprosthetics. Theory and Practice, vol. 2 World Scientific, New Jersey (2004), pp. 844-877.

(56) References Cited

OTHER PUBLICATIONS

Kilgore, K. L. et al., "Block of Nerve Conduction Using High Frequency Alternating Current," $9^{th}$ Annual Conference of the International FES Society, Sep. 2004, Bournemouth, UK (2004).

Kralj, a. R. et al. "Functional Electrical Stimulation: Standing and Walking after Spinal Cord Injury," CRC Press, Boca Raton, FL (1989), pp. 1-15.

Landau, B. et al., "Neuromodulation techniques for medically refractory chronic pain," Annu Rev Med vol. 44 (1993), pp. 279-287.

Marsolais et al., "Implantation techniques and experience with percutaneous intramuscular electrodes in the lower extremities," Journal of Rehabilitation Research and Development, Veterans Administration, vol. 3, No. 3, pp. 1-8.

Masini et al., "Activated Pyrolytic Carbon Tip Pacing Leads: An Alternative to Steroid—Eluting Pacing Leads?" Pacing and Clinical Electrophysiology, vol. 19, No. 11 (Nov. 1996), pp. 1832-1835.

McCREERY, D. et al., "Charge Density and Charge Per Phase as Cofactors in Neural Injury Induced by Electrical Stimulation," IEEE Transactions on Biomedical Engineering, vol. 37, No. 10 (Oct. 1990), pp. 996-1001.

Melzack et al., "Pain Mechanisms: A New Theory," Science, vol. 150 (Nov. 19, 1965), No. 3699, pp. 971-979.

Merrill, D. et al., "Electrical stimulation of excitable tissue: design of efficacious and safe protocols," Journal of Neuroscience Methods vol. 141 (2005), pp. 171-198.

Peckham et al., "Restoration of key grip and release in the C6 tetraplegic patient through functional electrical stimulation," The Journal of Hand Surgery, vol. 5, No. 5 (Sep. 1980), pp. 462-469.

Peckham, P. H. et al., "Implantable Neuroprosthesis Research G Efficacy of an implanted neuroprosthesis for restoring hand grasp in tetraplegia: A multicenter study," Archives of Physical Medicine & Rehabilitation vol. 82 (2001), pp. 1380-1388.

Prochazka, a. et al., "The bionic glove: An electrical stimulator garment that provides controlled grasp and hand opening in quadriplegia," Arch. Phys. Med. Rehabil. vol. 78 (1997), pp. 608-614.

Prochazka et al., "Clinical experience with reinforced, anchored intramuscular electrodes for functional neuromuscular stimulation," Journal of Neuroscience Methods, vol. 42 (1992), pp. 175-184.

Scheiner, a. et al., "Imbalanced Biphasic Electrical Stimulation: Muscle Tissue Damage," Annals of Biomedical Engineering (1990), vol. 18, pp. 407-425.

Shaker, H. et al., "Sacral root neuromodulation in the Treatment of Various Voiding and Storage Problems," International Urogynecology Journal vol. 10 (1999), pp. 336-343.

Shaker, H. S. et al., "Reduction of bladder outlet resistance by selective sacral root stimulation using high—frequency blockade in dogs: an acute study," J Urol 160 (3 Pt 1) (1997), pp. 901-907.

Skold, C. et al., "Spasticity After Traumatic Spinal Cord Injury: Nature, Severity, and Location," Arch Phys. Med. Rehabil, vol. 80 (Dec. 1999), pp. 1548-1557.

Solomonow, M. et al., "Control of muscle contractile force through indirect high-frequency stimulation," Am J. Phys. Med., vol. 62 (1983), pp. 71-82.

Strojnik, P. et al., "Treatment of drop foot using an implantable peroneal underknee stimulator," Scandanavian J. Of Rehabil. Med., vol. 19 (1987), pp. 37-43.

Stoykov et al., "Recording Intramuscular EMG Signals Using Surface Electrodes, 2005 IEEE 9th International Conference on Rehabilitation Robotics," Jun. 28—Jul. 1, 2005, Chicago, IL, pp. 291-294.

Tagusari et al., "Fine Trabecularized Carbon: Ideal Material and Texture for Percutaneous Device System of Permanent Left Ventricular Assist Device. Artificial Organs," vol. 22, No. 6 (Jun. 1998), pp. 481-487.

Tai, C. et al., "Block of external urethral sphincter contradiction by high frequency electrical stimulation of pudendal nerve," J Urol, vol. 172 (5 Pt 1) (2004), pp. 2069-2072.

Tai, C. et al., "Response of external urethral sphincter to high frequency biphasic electrical stimulation of pudendal nerve," J Urol, vol. 174(2) (2005), pp. 782-786.

Tai, C. et al., "Voiding Reflex in Chronic Spinal Cord Injured Cats Induced by Stimulating and Blocking Pudendal Nerves," Department of Pharmacology, University of Pittsburgh (2007), Neurourology and Urodynamics 26, pp. 879-886.

Van Heeckeren, D.W. et al., "Electrophrenic respiration by radiofrequency induction," Journal of Thoracic & Cardiovascular Surgery, vol. 52 (1966), pp. 655-665.

Vodovnik, L., "Therapeutic effects of functional electrical stimulation of extremities," Medical and Biological Engineering & Computing, vol. 19 (1981), pp. 470-478.

Walker, J. et al., "Fundamentals of Physics," New Jersey, Hoboken, (2007), pp. 791-817.

Waltz, J. M., "Spinal cord stimulation: a quarter century of development and investigation. A review of its development and effectiveness in 1,336 cases," Stereotactic & Functional Neurosurgery, vol. 69 (1997), pp. 288-299.

Whitwam, J. G. et al., "The Use of Direct Current to Cause Selective Block of Large Fibres in Peripheral Nerves," Br. J. Anaesth. (1975), vol. 47, pp. 1123-1133.

Woo, R., "Spasticity: Orthopedic Perspective," (2001) Special Article, Journal of Child Neurology, vol. 16, No. 1, pp. 47-53.

Yu, D. T. et al., "Percutaneous intramuscular neuromuscular electric stimulation for the treatment of shoulder subluxation and pain in patients with chronic hemiplegia: a pilot study," Arch Phys. Med. Rehabil, vol. 82 (1997), pp. 20-25.

METHOD OF ROUTING ELECTRICAL CURRENT TO BODILY TISSUES VIA IMPLANTED PASSIVE CONDUCTORS

CROSS REFERENCE TO RELATED APPLICATIONS

This application is a Continuation of U.S. patent application Ser. No. 13/850,760, entitled "Method of Routing Electrical Current To Bodily Tissues Via Implanted Passive Conductors," filed Mar. 26, 2013, which is a Continuation of U.S. patent application Ser. No. 12/400,202, filed Mar. 9, 2009, now U.S. Pat. No. 8,406,886, which is a Continuation of U.S. patent application Ser. No. 11/337,824, filed Jan. 23, 2006, now U.S. Pat. No. 7,502,652, which is a Continuation-in-Part of International Application No. PCT/CA2005/000074 filed Jan. 24, 2005, which claims priority from U.S. Provisional Application No. 60/538,618 filed Jan. 22, 2004. Each of the aforementioned applications is incorporated herein in its entirety by reference.

BACKGROUND

The present invention relates to an implant, system and method for treating a disorder of the nervous system in a subject. The method involves using passive electrical conductors which route electrical current to electrically stimulate a target body tissue to either activate or block neural impulses depending upon the frequency and the disorder to be treated.

Nerve cells consist of an axon for transmitting action potentials or neural impulses, and dendrites for receiving such impulses. Normally, nerves transmit action potentials from the impulse-sending axon of one nerve cell to the impulse-receiving dendrites of an adjacent nerve cell. At synapses, the axon secretes neurotransmitters to trigger the receptors on the next nerve cell's dendrites to initiate a new electrical current.

In some pathological states, transmission of action potentials is impaired; thus, activation of neural impulses is required to restore normal functioning. Electrically-excitable bodily tissues such as nerves and muscles may be activated by an electrical field applied between electrodes applied externally to the skin. Electric current flows through the skin between a cathode electrode and an anode electrode, eliciting action potentials in the nerves and muscles underlying the electrodes. This method has been used for many years in different types of stimulators, including transcutaneous electrical nerve stimulators (TENS) which relieve pain, therapeutic electrical stimulators which activate muscles for exercise purposes (Vodovnik, 1981), functional electrical stimulators which activate muscles for tasks of daily life (Kralj et al., 1989); U.S. Pat. No. 5,330,516 to Nathan; U.S. Pat. No. 5,562,707 to Prochazka et al.) and stimulators that promote regeneration of damaged bones.

In other pathological states, action potentials are transmitted which do not serve a useful purpose; hence, blocking of unnecessary neural impulses is required to restore normal functioning. It has been reported that high-frequency stimulation can produce temporary reversible blocks of nerve axons (Solomonow et al., 1983; Tai et al., 2004; Bhadra and Kilgore, 2005). Generally, the frequency range is between 500 and 30,000 Hz.

Stimulation of nerves to either active or block neural impulses is typically achieved with the use of an implanted stimulator (also known as a neural prosthesis or neuroprosthesis) (Peckham et al., 2001; Horch and Dhillon, 2004). Neural prostheses have been developed to restore hearing, to restore movement in paralyzed muscles, to modulate activity in nerves controlling urinary tract function and to suppress pain and tremor. In some cases, neural prostheses are designed to inhibit or suppress unwanted neural activity, for example to block pain sensation or tremors. However, all neural prostheses intended for long-term use require the implantation of a stimulator that contains electronic components and often a battery. In the case of pain and tremor suppression, the activated nerves reflexly inhibit the activity of neural circuits within the central nervous system. This indirect mode of reducing unwanted neural activity is sometimes called neuromodulation (Landau and Levy, 1993; Groen and Bosch, 2001).

Surface electrical stimulators are used reflexly for example to reduce spastic hypertonus (Vodovnik et al., 1984; Apkarian and Naumann, 1991). A disadvantage of stimulation through electrodes attached to the body surface is that many non-targeted tissues may be co-activated along with the targeted tissues. This lack of selectivity often causes unwanted sensations and/or unwanted movements. Furthermore, tissues that lie deep within the body are difficult or impossible to stimulate adequately, because most of the electrical current flowing between the electrodes flows through tissues closer to the electrodes than the targeted tissues. Selectivity may be improved by implanting wires within the body that route electrical current from a stimulator to the vicinity of the targeted tissues. This method is used in cardiac pacemakers (Horch et al., 2004), dorsal column stimulators (Waltz, 1997), deep brain stimulators (Benabid et al., 1987) and sacral root stimulators (Brindley et al., 1982). Cuffs containing the uninsulated ends of the wires may be placed around peripheral nerves to restrict most of the current to the vicinity of the nerve and limiting the spread of current to surrounding tissues, thereby improving selectivity (Haugland et al., 1999). Generally when wires are implanted, the stimulators, complete with an energy source, are also implanted (Strojnik et al., 1987). Implanted stimulators are expensive and often require a controller and/or power source external to the body. Batteries within the implanted stimulators need periodic replacement, entailing surgery.

In a minority of cases, stimulating wires are implanted in bodily tissues and led through the skin (percutaneously) to a connector attached to the surface of the body, to which an external stimulator is attached (Peckham et al., 1980; Handa et al., 1998; Shaker and Hassouna, 1999; Yu et al., 2001). External stimulators are much less expensive than implanted stimulators, but the percutaneous wires provide a conduit for infection and therefore require daily cleaning and maintenance. This has generally limited the use of percutaneous electrodes to short-term applications. There is a need for a system which overcomes such problems and has the capability of activating or blocking nerve impulses depending upon the disorder to be treated.

SUMMARY

The present invention broadly relates to an implant, system and method using passive electrical conductors which route electrical current to electrically stimulate a target body tissue to either activate or block neural impulses depending upon the frequency and the disorder to be treated.

In one aspect, the present invention broadly provides an implant for electrically stimulating a target body tissue in a subject, the implant, once implanted, providing a conductive pathway for at least a portion of the electrical current flowing between surface cathodic and anodic electrodes positioned in spaced relationship on the subject's skin and transmitting that portion of the electrical current to the target body tissue, the implant comprising:

a passive electrical conductor of sufficient length to extend, once implanted, from subcutaneous tissue located below the surface cathodic electrode to the target body tissue, the electrical conductor having a pick-up end and a stimulating end and being insulated between its ends, the pick-up end forming an electrical termination having a sufficient surface area to allow a sufficient portion of the electrical current to flow through the conductor, in preference to flowing through body tissue between the surface cathodic and anodic electrodes, such that the target body tissue is stimulated, and the stimulating end forming an electrical termination for delivering the portion of electrical current to the target body tissue.

In another aspect, the invention provides a system for electrically stimulating a target body tissue in a subject comprising the above implant, together with surface cathodic and anodic electrodes for making electrical contact with the subject's skin, and which, when positioned in spaced relationship on the subject's skin, for transmitting electrical current to the target body tissue; and a stimulator external to the subject's body, electrically connected to the surface cathodic and anodic electrodes, the stimulator supplying direct, pulsatile, or alternating current to the surface cathodic and anodic electrodes.

In another aspect, the invention provides a method for electrically stimulating a target body tissue in a subject comprising the steps of:

providing the above implant;

implanting the implant entirely under the subject's skin, with the pick-up end positioned in subcutaneous tissue located below the surface cathodic electrode, and the stimulating end positioned proximate to the target body tissue;

positioning the surface cathodic and anodic electrodes in spaced relationship on the subject's skin, with the surface cathodic electrode positioned over the pick-up end of the electrical conductor so the portion of the current is transmitted through the conductor to the target body tissue, and so that the current flows through the target body tissue and returns to the anodic surface electrode through body tissues or through an implanted electrical return conductor extending between the target body tissue and subcutaneous tissue located below the surface anodic electrode; and applying direct, pulsatile or alternating electrical current between the surface cathodic electrode and the surface anodic electrode to cause the portion of the electrical current to flow through the implant sufficient to stimulate the target body tissue.

In yet another aspect, the present invention provides a method of treating a disorder in a subject comprising the steps of:

providing an implant to act as a conductive pathway for at least a portion of the electrical current flowing between surface cathodic and anodic electrodes positioned in spaced relationship on the subject's skin and transmitting the portion of the electrical current to the target body tissue, the implant comprising a passive electrical conductor of sufficient length to extend, once implanted, from subcutaneous tissue located below the surface cathodic electrode to the target body tissue, the electrical conductor having a pick-up end and a stimulating end and being insulated between its ends, the pick-up end forming an electrical termination having a sufficient surface area to allow a sufficient portion of the electrical current to flow through the conductor, in preference to flowing through body tissue between the surface cathodic and anodic electrodes, such that the target body tissue is blocked, and the stimulating end forming an electrical termination for delivering the portion of electrical current to the target body tissue;

implanting the implant entirely under the subject's skin, with the pick-up end positioned in subcutaneous tissue located below the surface cathodic electrode, and the stimulating end positioned proximate to the target body tissue;

positioning the surface cathodic and anodic electrodes in spaced relationship on the subject's skin, with the surface cathodic electrode positioned over the pick-up end of the electrical conductor so the portion of the current is transmitted through the conductor to the target body tissue, and so that the current flows through the target body tissue and returns to the anodic surface electrode through body tissues or through an implanted electrical return conductor extending between the target body tissue and subcutaneous tissue located below the surface anodic electrode; and applying electrical current between the surface cathodic electrode and the surface anodic electrode in the form of a cyclical waveform at a frequency capable of blocking the target body tissue so as to treat the disorder.

As used herein and in the claims, the terms and phrases set out below have the following definitions.

"Blocking" or "block" is meant to refer to preventing the conduction or propagation of action potentials or nerve impulses along the axons of a target nerve partially or completely.

"Body tissue" is meant to refer to a neural tissue (in the peripheral or central nervous system), a nerve, a muscle (skeletal, respiratory, or cardiac muscle) or an organ, for example, the brain, cochlea, optic nerve, heart, bladder, urethra, kidneys and bones.

"Cyclical waveform" means any form of electrical current in a repeating waveform without limitation to its shape or form, including without limitation alternating current, pulsatile, sinusoidal, triangular, rectangular and sawtooth waveforms.

"Disorder" is meant to include movement disorders, muscular disorders, incontinence, urinary retention, pain, epilepsy, cerebrovascular disorders, sleep disorders, autonomic disorders, disorders of vision, hearing and balance, and neuropsychiatric disorders.

"Electrical current" is meant to refer to current applied at the surface of the skin that is resistively and capacitively coupled to the implanted passive conductor, which in turn conveys the current to the target neural tissue.

"Subject" means an animal including a human.

BRIEF DESCRIPTION OF THE DRAWINGS

FIG. 5A shows the maximum decrease in urethral pressure elicited by stimulation of the pudendal nerve at different amplitudes and frequencies, with the maximum decrease defined as the difference between the intraurethral pressure just prior to and during high frequency stimulation. FIG. 5B shows the difference between background intraurethral pressure and the intraurethral pressure obtained during high frequency stimulation at different amplitudes and frequencies.

DETAILED DESCRIPTION

The invention broadly provides an implant for electrically stimulating a target body tissue in a subject to either activate or block neural impulses depending upon the frequency and the disorder to be treated. Once implanted, the implant provides a conductive pathway for at least a portion of the electrical current flowing between surface cathodic and anodic electrodes positioned in spaced relationship on a subject's skin, and transmits that portion of electrical current to the target body tissue to either activate or block neural impulses. In further aspects, the invention provides a system and method incorporating the implant.

The subject can be an animal including a human. The body tissue can be a neural tissue (in the peripheral or central nervous system), a nerve, a muscle (skeletal, respiratory, or cardiac muscle) or an organ, for example, the brain, cochlea, optic nerve, heart, bladder, urethra, kidneys and bones.

The invention can be applied to treat various conditions in which stimulation to either activate or block neural impulses is required. Such conditions can include movement disorders (e.g., spasticity, hypertonus, rigidity, tremor and/or muscle weakness, Parkinson's disease, dystonia, cerebral palsy), muscular disorders (e.g., muscular dystrophy), incontinence (e.g., urinary bladder disorders), urinary retention, pain (e.g., migraine headaches, neck and back pain, pain resulting from other medical conditions), epilepsy (e.g., generalized and partial seizure disorder), cerebrovascular disorders (e.g., strokes, aneurysms), sleep disorders (e.g., sleep apnea), autonomic disorders (e.g., gastrointestinal disorders, cardiovascular disorders), disorders of vision, hearing and balance, and neuropsychiatric disorders (e.g., depression). The invention may also be used for promoting bone growth (as required, for example, in the healing of a fracture), wound healing or tissue regeneration.

For stimulation of a target body tissue, particular frequencies to be applied depend upon many factors; for example, the type of nerve to be blocked, the tissue which the nerve innervates, the size of the nerve, the subject to be treated, the type of condition, the severity of the condition, and the receptiveness of the subject to the treatment. In general, for blocking, high frequencies are useful, for example, the cyclical waveform can be applied at a frequency in the range of between 100 and 30,000 Hz, or alternatively in the range of between 100 and 20,000 Hz. Still alternatively, the cyclical waveform can be applied at a frequency in the range of between 100 and 10,000 Hz, or in the range between 200 and 5,000 Hz. For activation, low frequencies are generally used, for example, a frequency in the range of between 1 and 100 Hz, or alternatively, in the range of between 1 and 50 Hz. Still alternatively, the frequency can be in the range of between 1 and 20 Hz.

A. The Router System

Figure 1:
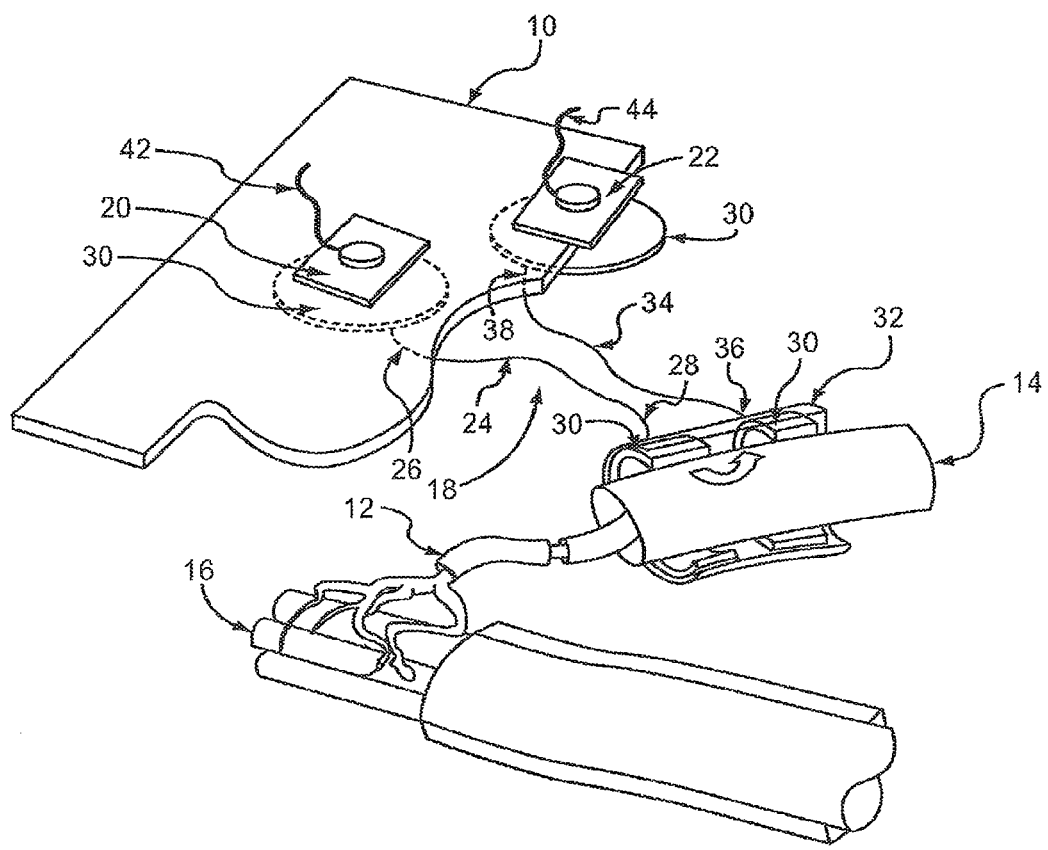
FIG. 1 is a schematic three-dimensional view of an embodiment of the invention having an implanted electrical conductor, surface cathodic and anodic electrodes, and an implanted electrical return conductor.

The invention is described with reference to the drawings in which like parts are labeled with the same numbers in FIGS. 1 to 4. The invention is shown generally in FIG. 1 which schematically illustrates portions of a subject's body tissues, including skin 10, a nerve 12 with its overlying nerve sheath 14, and a muscle 16. FIG. 1 also illustrates an implant indicated generally at 18, a surface cathodic electrode 20 and a surface anodic electrode 22. The implant 18 is provided for electrically stimulating a target body tissue, such as a nerve 12, in a subject to either activate or block neural impulses. Once implanted, the implant 18 provides a conductive pathway for at least a portion of the electrical current flowing between the surface cathodic and anodic electrodes 20, 22.

When positioned in spaced relationship on the subject's skin 10, the surface cathodic and anodic electrodes 20, 22 make electrical contact with the skin 10 and transmit electrical current to the target body tissue. Surface cathodic and anodic electrodes 20, 22 can be selected from a conductive plate or sheet, a conductive gel electrode, a conductive rubber or polymer electrode that may be partially coated with an electrode paste or gel, or a moistened absorbent pad electrode. Self-adhesive hydrogel electrodes of the type used to stimulate muscles, with surface areas of 1 square centimeter or more are particularly effective. Platinum iridium electrodes, which are composed typically of 80% or more platinum and 20% or less iridium, can also be used (for example, 85% platinum-15% iridium alloy; 90% platinum-10% iridium alloy). The positions of the surface cathodic and anodic electrodes 20, 22 on the skin 10 may vary, depending upon the location and nature of the target body tissue.

A plurality of surface electrodes 20, 22 may be fabricated on a single non-conductive substrate to form an electrode array that may be conveniently attached to the skin 10 in one maneuver. Similarly, the plurality of terminations 30 of implanted conductors 24 may be fabricated on a substrate to form an array. By matching the physical layout of the surface electrode array to that of the implanted terminations array, a good spatial correspondence of surface and implanted conductors may be achieved in a convenient and reproducible manner. Surface electrode arrays in which the conductivity of each element of the array may be independently controlled could also be used to adjust the conductivity between the surface electrodes and the terminations in an implanted array.

The implant 18 comprises a passive electrical conductor 24 of sufficient length to extend, once implanted, from subcutaneous tissue located below the surface cathodic electrode 20 to the target body tissue, for example nerve 12. The electrical conductor 24 can be formed from a metal wire, carbon fibers, a conductive rubber or other conductive polymer, or a conductive salt solution in rubber. Multistranded, TEFLON®-insulated, stainless-steel wire conductors of the type used in cardiac pacemaker leads have been found to be particularly effective. MP35N® alloy (a nonmagnetic, nickel-cobalt-chromium-molybdenum alloy) which is commonly used in parts for medical applications is also suitable. The electrical conductor has a pick-up end 26 and a stimulating end 28, and is insulated between its ends 26, 28.

The electrical impedance of the interface between the ends 26, 28 of the conductor 24 (when implanted) and the surrounding body tissue may be reduced by enlarging the surface area of the ends 26, 28. For that purpose, one or both of the pick-up and stimulating ends 26, 28 form electrical terminations 30 having sufficient surface areas for reducing the electrical impedance of the interface between the pick-up and stimulating ends 26, 28 of the electrical conductor 24 and the surrounding body tissues. Preferably, the pick-up end 26 forms a termination 30. The pick-up end 26 forms an electrical termination 30 which has a sufficient surface area to allow a sufficient portion of the electrical current to flow through the electrical conductor 24, in preference to flowing through body tissue between the surface cathodic and anodic electrodes 20, 22, such that the target body tissue is stimulated to either activate or block neural impulses. The stimulating end 28 also forms an electrical termination 30 for delivering the portion of electrical current to the target body tissue (i.e., nerve 12).

Terminations 30 should have sufficient surface area for providing high conductivity contact with body tissues, and lowering the electrical impedance between the body tissue and the conductor. If the surface area is minimal, the amount of current flowing through a conductor to the termination is reduced to an ineffective amount. The surface area required may thus be determined by a knowledge of the electrical impedance of the interface between the tissue and the terminations 30 at the receiving and stimulating ends 26, 28. Beneficial results have been obtained by making the surface area of metal terminations 30 at the ends 26, 28 about 0.5 cm$^2$. The electrical impedance of each interface between tissue and terminations 30 at ends 26, 28 was then about 5 times the electrical impedance of all the subcutaneous tissue between surface electrodes 20, 22. A typical value of tissue impedance is 200 ohms. The impedance of the conductor itself is chosen to be very small, for example 5 ohms. In the example just given, the sum of the two interface impedances of the terminations 30 plus the conductor impedance was about 2000 ohms, that is to say about ten times the tissue impedance. Thus about 10% of the current applied between surface electrodes 20, 22 flows through conductor 24 to the target tissue. In the case of the target tissue being a nerve 12 supplying a muscle 16, the amount of current between surface electrodes 20, 22 required to produce a useful muscle contraction of the target muscle 16 then remains below the threshold level of activation of nerve endings in the subcutaneous tissue immediately between surface electrodes 20, 22. This is a beneficial relationship, because it means that target muscles 16 can be activated with little or no local sensation under the surface electrodes 20, 22.

Terminations 30 of various shapes, materials and spatial arrangements can be used; for example, terminations 30 can provide an enlarged surface in the form of a coil, spiral, cuff, rod, or a plate or sheet in the form of an oval or polygon. As an example, FIG. 1 illustrates a termination 30 as a plate or sheet in the form of an oval at the pick-up end 26 of the electrical conductor 24, and in the form of a cuff at the stimulating end 28. The cuff or a portion thereof can encircle or partially encircle the entirety or part of the nerve sheath 14 of the nerve 12. The cuff or a portion thereof can be positioned proximate to the nerve sheath 14, or the inner surface of the cuff or a portion thereof can directly contact the nerve sheath 14.

Beneficial results are obtained with stainless-steel plates or sheets in the form of an oval which is about 0.5 cm$^2$ in area and 1 mm thick, or made of metal foil and stainless-steel mesh and being about 0.5 cm$^2$ in surface area and 0.3 mm thick. For terminations 30 of conductors with nerve cuffs, nerve cuffs made of metal foil or stainless-steel mesh and being 0.5 to 1 cm$^2$ in surface area and 0.3 mm thick are suitable. Further, silastic elastomer cuffs ranging from 5 mm to 15 mm in length, 4 mm to 6 mm inside diameter, and 1 mm thick are suitable.

Terminations 30 can be formed from uninsulated ends 26, 28 of the electrical conductor 24, or from other conductive or capacitive materials. Terminations 30 can be formed by coiling, spiraling or weaving long, uninsulated lengths of the pick-up or stimulating ends 26, 28 to provide a sufficient surface. The surface area of the termination is thus "enlarged" relative to the surface area of a shorter length of the electrical conductor 24. This raises the effective surface area of the terminations 30 within a small space to provide higher conductivity contact with body tissues, and to lower the electrical impedance between the body tissue and the conductor 24 to allow current flow in the conductor in preference to in the body tissue. Sufficient current flow is thereby provided in the conductor 24 to stimulate the target tissue. Alternatively, prefabricated terminations 30 (for example, plates or sheets in the form of ovals or polygons) can be attached directly to the pick-up and stimulating ends 26, 28. Further, terminations 30 can be coated or modified with conductive materials to maximize the flow of electrical current through the target body tissue.

The spatial arrangement of the terminations 30 can be varied; for example, multiple terminations 30 can also be applied to different parts of a body tissue (Grill et al., 1996). Advantageously, the terminations 30 themselves can be in the form of closely-spaced contacts enclosed within an embracing cuff 32 placed around the nerve 12. The embracing cuff 32 can be formed from conductive silicone rubber.

Electrical impedance may be further reduced by providing conductive or capacitive coatings, or an oxide layer on the terminations 30. The coating can be selected from a material whose structural or electrical properties improve the electrical conductance between the tissue and the conductor, for example, by providing a complex surface into which tissue can grow (for example, a polymer such as poly-diethoxythiophene, or suitable oxide layers including tantalum and sintered iridium). In addition, the terminations 30 can have coatings which provide an anti-inflammatory, anti-bacterial or tissue ingrowth effect. The coating can be a substance selected from an anti-inflammatory agent, antibacterial agent, antibiotic, or a tissue ingrowth promoter.

Optionally, performance of the invention can be improved by implanting an electrical return conductor 34 of sufficient length to extend from the target body tissue to subcutaneous tissue located below the surface anodic electrode 22. The electrical return conductor 34 provides a low-impedance conductive pathway from the target body tissue to the surface anodic electrode 22, thereby concentrating the electric field through the target tissue. The electrical return conductor 34 can be formed from a metal wire, carbon fibers, a conductive rubber or other conductive polymer, or a conductive salt solution in rubber. The electrical return conductor 34 has a collecting end 36 and a returning end 38, and is insulated between its ends 36, 38. Both the collecting end 36 and the returning end 38 form electrical terminations 30 (as described above) for reducing the electrical impedance of the interface between the collecting end 36 and returning end 38 of the electrical return conductor 34 and the surrounding body tissues. The collecting end 36 forms an electrical termination 30 (shown in FIG. 1 in the form of a cuff), which has a sufficient surface area to allow a portion of the electrical current delivered to the target body tissue to return through the electrical return conductor 34 in preference to returning through body tissue. The returning end 38 forms an electrical termination 30 (shown in FIG. 1 as a plate or sheet in the form of an oval) which returns the electrical current to the surface anodic electrode 22 via the subcutaneous tissue and skin underlying the surface anodic electrode 22.

A power source 40 (shown in FIGS. 2-4) provides operating power to a stimulator (not illustrated) which is external to the subject's body. The stimulator is electrically connected to the surface cathodic and anodic electrodes 20, 22 to supply electrical current to the surface cathodic and anodic electrodes 20, 22. The current can be resistive or capacitive, depending on the net impedance encountered between the electrodes 20, 22.

Although most of the electrical current flows through the body tissues in proximity to the surface cathodic and anodic electrodes 20, 22, there is flow of electrical current through the electrical conductor 24, nerve 12, and electrical return conductor 34. As shown in FIG. 1, the surface cathodic electrode 20 is positioned over the pick-up end 26 of the electrical conductor 24, so that a portion of the current is transmitted through the conductor 24 to the target body tissue, and current flows through the target body tissue and returns to the anodic surface electrode 22 through body tissues. This can also be achieved through the implanted electrical return conductor 34 extending between the target body tissue and subcutaneous tissue located below the surface anodic electrode 22.

The complete electrical path of the portion of the electrical current is as follows: cathodic wire 42, surface cathodic electrode 20, skin 10, termination 30, pick-up end 26, electrical conductor 24, stimulating end 28, termination 30, nerve sheath 14, nerve 12, termination 30, collecting end 36, electrical return conductor 34, returning end 38, termination 30, skin 10, surface anodic electrode 22 and anodic wire 44. The pulses of electrical current can elicit action potentials which are conducted along nerve 12 to muscle 16, causing it to contract. Alternatively, electrical current in the form of high frequency waveforms can block action potentials conducted along nerve 12 to muscle 16 to prevent muscle contractions.

Various disorders are amenable to treatment by the invention as shown in FIG. 1. As described below, the implanted passive electrical conductors of the present invention are capable of routing electrical current to stimulate various target body tissues to either activate or block neural impulses depending upon the frequency and disorder to be treated. Applications have been provided below to illustrate examples of target body tissues and disorders for which the invention is beneficial.

B. Activation of Neural Impulses Using the Router System

In some pathological states, transmission of action potentials is impaired; thus, activation of neural impulses is required to restore normal functioning. In the present invention, the stimulator can supply direct, pulsatile or alternating current between the surface cathodic and anodic electrodes 20, 22 to cause the portion of the electrical current to flow through the implant 18 sufficient to stimulate the target body tissue to activate neural impulses.

Exemplary pulse parameters of electrical current flowing between the surface cathodic and anodic electrodes 20, 22 for activation of neural impulses are as follows: biphasic current pulses, 30 pulses per second, each phase 200 microseconds in duration, and a peak current per pulse ranging from 0.7 to 2 milliampere. Beneficial results can be obtained with rectangular, feedback-controlled current pulse waveforms, although other waveforms and modes of control of current or voltage have also been found to give satisfactory results. The inventor has discovered that between 10% and 20% of the current flowing between the surface electrodes 20, 22 is propagated through an implanted conductor 24, even when there is no electrical return conductor 34. The type of current may be dependent upon the application for which the invention is intended; for example, continuous current would be applied, rather than pulsatile current, when the target body tissue is bone and promotion of bone growth is desired.

As is known to those skilled in the art, the electric currents delivered by a pulse generator to a plurality of electrodes 20, 22 may be independently controlled with the use of an interleaved pulse train. This comprises a sequence of stimulus pulses of different amplitudes, the pulses separated in time by a few milliseconds and delivered to each electrode in turn, the sequence as a whole being repeated at a rate such as 30 times per second. The amplitudes of the pulses flowing through each electrode may thereby be controlled independently.

For activation, low frequencies are generally used, for example, a frequency in the range of between 1 and 100 Hz, or alternatively, in the range of between 1 and 50 Hz. Still alternatively, the frequency can be in the range of between 1 and 20 Hz.

Figure 2:
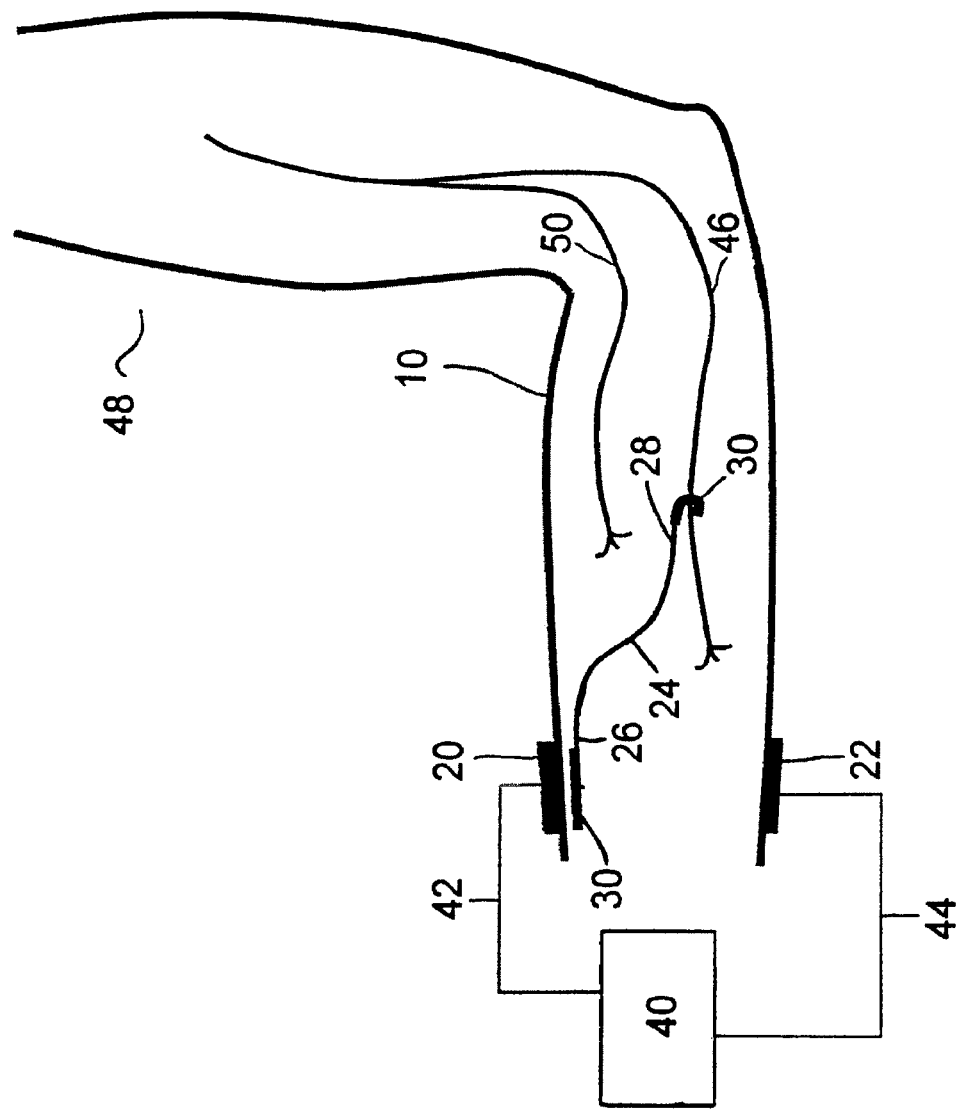
FIG. 2 is a side elevation view, in section, of an embodiment of the invention having an implanted electrical conductor and surface cathodic and anodic electrodes.

As an example, FIG. 2 illustrates the invention for use in the treatment of a movement disorder requiring activation of the median nerve 46. The median nerve 46 innervates most of the flexor muscles in front of the forearm, most of the short muscles of the thumb, and the short muscles of the hand. A subject's arm 48 is illustrated with the implant 18 implanted in the forearm. The electrical conductor 24 is illustrated with its pick-up end 26 forming a termination 30 for receiving the electrical current from the surface cathodic electrode 20. The stimulating end 28 forms a termination 30 for delivering the electrical current to the median nerve 46. A surface anodic electrode 22 is positioned on the skin 10. A flow of electrical current from the power source 40 is supplied via cathodic wire 42 into the skin 10 at the surface cathodic electrode 20 and the surface anodic electrode 22 via anodic wire 44. The electrical current flows through the termination 30, the pick-up end 26, the electrical conductor 24, the stimulating end 28, a portion of the median nerve 46, the tissue between stimulating end 28 and surface anodic electrode 22 including the skin underlying electrode 22, the surface anodic electrode 22, anodic wire 44 and the power source 40, thus completing the electrical circuit. Some of the current flowing between the stimulating end 28 and the surface anodic electrode 22 passes through the target body tissue (in this example, median nerve 46), thereby causing the muscle 16 of the arm 48 to be stimulated.

Figure 3:
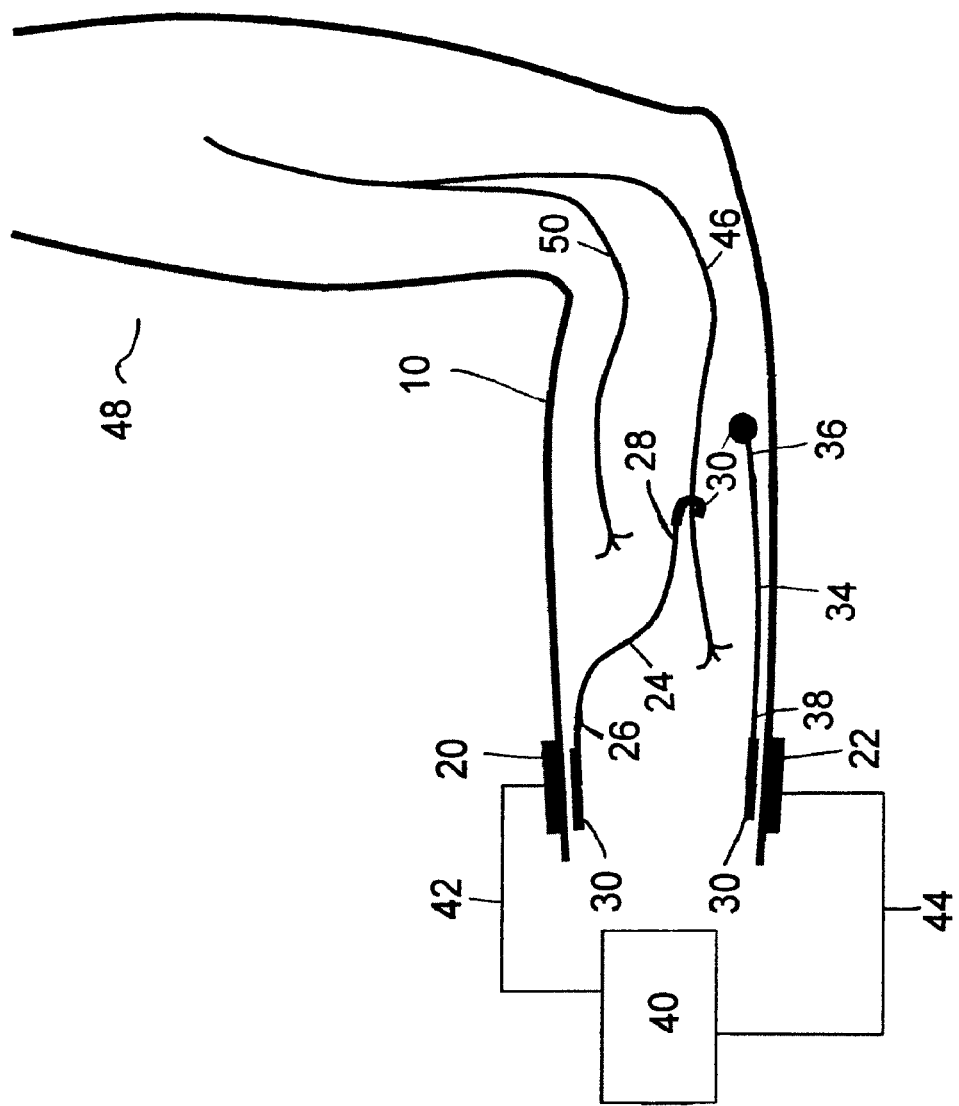
FIG. 3 is a side elevation view, in section, of an alternate embodiment of the invention having an implanted electrical conductor, surface cathodic and anodic electrodes, and an electrical return conductor.

As a further example, FIG. 3 again illustrates the invention for use in the treatment of a movement disorder requiring activation of the median nerve 46. However, in addition to the components shown in FIG. 2, FIG. 3 illustrates an electrical return conductor 34. The electrical circuit is essentially the same as that described for FIG. 2, with the exception that after flowing through the stimulating end 28 and the median nerve 46, the electrical current flows through termination 30, the collecting end 36, the electrical return conductor 34, the returning end 38, termination 30, the surface anodic electrode 22, anodic wire 44 and the power source 40, thus completing the electrical circuit. Advantageously, the electrical return conductor 34 acts to collect electrical current flowing through the target body tissue (i.e., median nerve 46) from the electrical conductor 24 and provides a low impedance pathway back to the surface anodic electrode 22, thereby concentrating the electric field through the target body tissue (i.e., median nerve 46).

Figure 4:
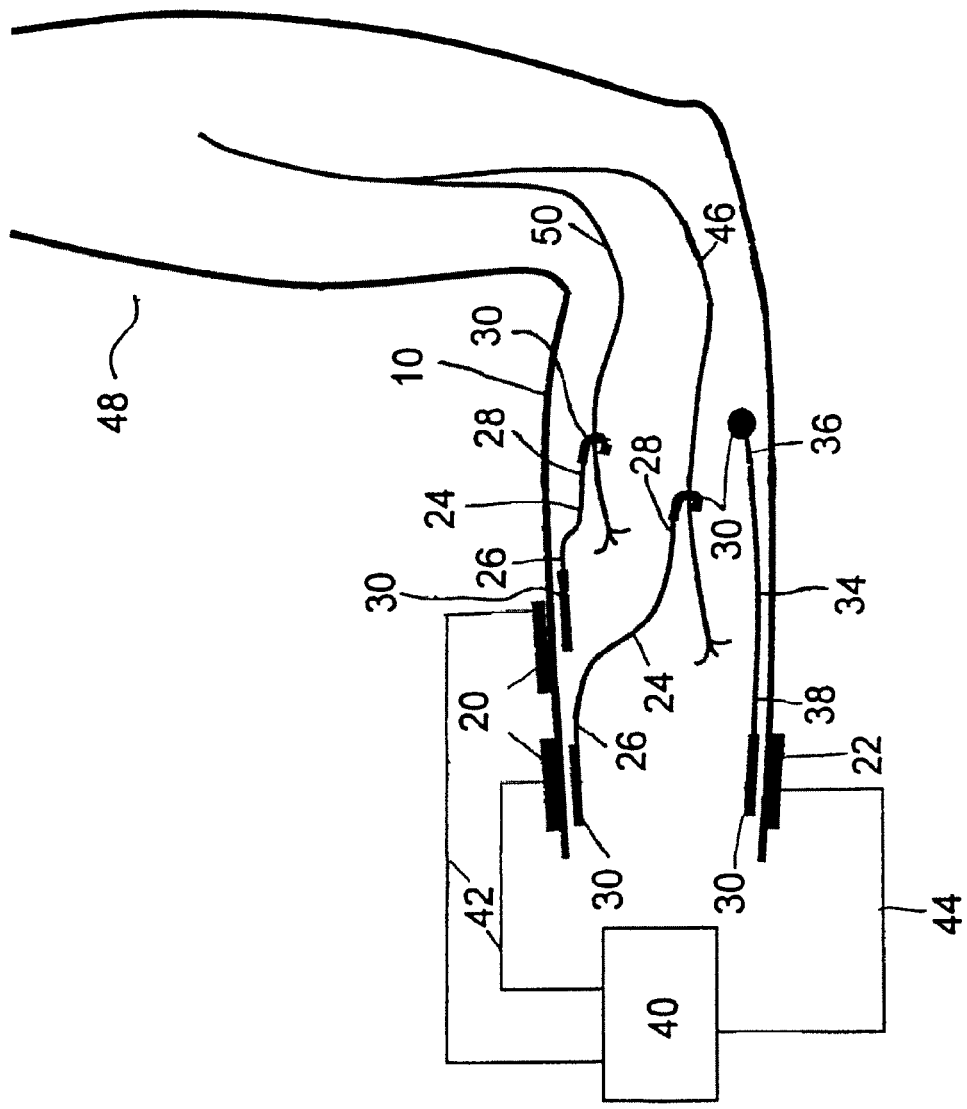
FIG. 4 is a side elevation view, in section, of an alternate embodiment of the invention having two implanted electrical conductors, two surface cathodic electrodes, an anodic electrode, and an electrical return conductor.

As yet a further example, FIG. 4 illustrates a plurality of implants 18 for electrically stimulating more than one target body tissue independently or in unison to activate neural impulses. Each implant 18 is implanted entirely under the subject's skin 10 and is of a sufficient length to extend to a different target body tissue. The presence of multiple implants 18 necessitates positioning of a plurality of surface cathodic electrodes 20, and one or more surface anodic electrodes 22 appropriately relative to the implants 18 to stimulate the different target body tissues independently or in unison. FIG. 4 illustrates the invention for use in the treatment of a movement disorder requiring stimulation of the median nerve 46 and the radial nerve 50. The radial nerve 50 innervates extensor muscles on the back of the arm and forearm, the short muscles of the thumb, and the extensor muscles of the index finger. Two separate surface cathodic electrodes 20 are each electrically connected via two separate cathodic wires 42 to a stimulator (not illustrated) operated by the power source 40. Electrical current is transmitted to the two separate electrical conductors 24, one of which extends to the median nerve 46, and the other to the radial nerve 50. An electrical return conductor 34 extends from the target tissue (i.e., below the median nerve 46) to subcutaneous tissue located below one surface anodic electrode 22.

The electrical path of the current is as follows: cathodic wire 42, the surface cathodic electrodes 20, the skin 10, termination 30, the pick-up end 26, the electrical conductor 24, the stimulating end 28, termination 30, the median nerve 46 and/or radial nerve 50, termination 30, collecting end 36, electrical return conductor 34, returning end 38, termination 30, surface anodic electrode 22, anodic wire 44, and power source 40. The median nerve 46 and radial nerve 50 can be stimulated either independently by pulsatile electrical current to provide firstly, a flexion or upward position of the wrist and finger closing (via the median nerve 46), then secondly, extension or downward position of the wrist and finger extension (via the radial nerve 50). Alternatively, the median nerve 46 and radial nerve 50 can be stimulated simultaneously for example, to straighten the hand (i.e., position the wrist horizontally). It will be appreciated by those skilled in the art that the invention can be applied to other target body tissues and disorders where activation of neural impulses is needed to restore normal functioning.

C. Blockade of Neural Impulses Using the Router System

In some pathological states, action potentials are transmitted which do not serve a useful purpose; hence, blocking of unnecessary nerve impulses is required to restore normal functioning. The invention provides a method for treating disorders by applying electrical current in the form of cyclical waveforms at a frequency capable of blocking a target body tissue so as to treat the disorder. Electrical current waveforms are generated at a frequency which is high enough to cause conduction block in target neural tissues. For example, the electrical current can be applied in the form of pulses, typically 20 to 1,000 microseconds in duration at a rate high enough to cause conduction block in the target axons. The frequency and pulse parameters, including pulse amplitude, pulse duration and pulse rate, depend upon many factors that are well known to those skilled in the art; for example, the type of nerve to be blocked (either in the peripheral or central nervous system), the tissue which the nerve innervates (e.g., autonomic organs such as the bladder, or somatic organs such as muscle), the size of the nerve, the subject to be treated, the type of condition, the severity of the condition, and the receptiveness of the subject to the treatment.

A wide range of frequencies from 100 Hz to 30 kHz has been reported to produce an effective block depending upon various parameters among those described above and the particular stimulation technique used; for example, 100-300 Hz for subthalamic nucleic in human deep brain to reduce motor symptoms (Ashkan et al., 2004; Filali et al., 2004); 500 Hz for a muscle nerve (Solomonow et al., 1983); 600 Hz for a sacral nerve root in an acute spinalized dog to achieve bladder voiding (Shaker et al., 1998); 600 Hz for the ventral sacral root to inhibit urethral sphincter contractions in chronically spinalized dogs (Abdel-Gawad et al., 2001); 200-1400 Hz for epidural stimulation in a human to moderate motor disorders (Broseta et al., 1987); 4 kHz for the pudendal nerve in cats to block external urethral sphincter contractions (Tai et al. 2004, 2005); and 10-30 kHz for a peripheral nerve to treat spasticity and pain (Bhadra and Kilgore, 2005).

For blockade of neural impulses, it is required that the frequency is higher than frequencies normally required to stimulate a nerve to conduct action potentials, and high enough to block conduction of action potentials in target body tissues. In general, for blocking, high frequencies are useful, for example, the cyclical waveform can be applied at a frequency in the range of between 100 and 30,000 Hz, or alternatively in the range of between 100 and 20,000 Hz. Still alternatively, the cyclical waveform can be applied at a frequency in the range of between 100 and 10,000 Hz, or in the range between 200 and 5,000 Hz.

Example 1 (see below) illustrates use of the present invention, the results of which suggest that stimulation with an amplitude greater than 3 mA and a frequency greater than 200 Hz is capable of blocking transmission of neural impulses in the pudendal nerve of a cat. It is highly advantageous that the stimulator of the invention is external to the subject's body and supplies high frequency electrical current waveforms to the surface cathodic and anodic electrodes 20, 22 positioned externally on the subject's skin. A wide range of pulse parameters can be readily and easily tested and adjusted to determine optimal parameters for achieving the desired physiological result in a subject following implantation of the electrical conductor 24.

Exemplary pulse parameters of high frequency trains of electrical current flowing between surface cathodic and anodic electrodes 20, 22 are as follows: current-controlled or voltage-controlled biphasic pulses, with phase durations ranging from 10 microseconds to 1,000 microseconds, or cyclical waveforms such as sinusoids or triangular, rectangular or sawtooth waveforms.

Blockade of a nerve impulse using the invention is reversible at all frequencies such that when high frequency stimulation is turned off, the nerve can again propagate action potentials and no damage has been incurred. Further, partial or complete blocking of a nerve impulse can be achieved depending upon the condition to be treated. For example, complete blocking of sensory nerves may be required to alleviate pain, while partial or complete blocking of sensory and motor nerves may be needed to reduce spasticity.

Other embodiments of the invention are possible. For instance, a plurality of implants 18 for electrically blocking more than one target body tissue independently or in unison can be used. The presence of multiple implants 18 necessitates positioning of a plurality of surface cathodic electrodes 20, and one or more surface anodic electrodes 22 appropriately relative to the implants 18 to block the different target body tissues independently or in unison.

In another embodiment, a plurality of implants 18 for electrically activating neural impulses in more than one body tissue independently or in unison can be used concomitantly with the above implants 18 for electrically blocking neural impulses in target body tissues. Two separate signals are required, with a low frequency signal required to activate a nerve, and a high frequency signal required to block another nerve. For example, bladder voiding can be achieved by applying low frequency pulse trains to the sacral nerve root S1, which elicits bladder and sphincter contractions, and by simultaneously applying high frequency waveforms to the pudendal nerve to block the sphincter contractions induced by stimulating the sacral nerve root S1.

Various disorders requiring blocking of neural impulses are amenable to treatment by the invention as shown in FIG. 1. As an example, the invention can be used to achieve bladder voiding (see Example 1). When the bladder is full, nerve signals are normally sent to the brain to convey the need to urinate. In response, the brain initiates a coordinated response in which the bladder wall contracts, creating pressure that forces urine into the urethra, while a sphincter, surrounding the urethra, opens to allow urine to flow out. In certain disorders, for example spinal cord injury, the bladder is generally unable to empty because of hyper-reflexive contractions of the external sphincter. The closure of the sphincter is maintained by reflexes intended to maintain continence, which can no longer be suppressed by signals from the brain. The pudendal nerve innervates the musculature of the pelvic floor and the external urethral and external anal sphincters. The motor component of the urinary branch of the pudendal nerve activates the external urethral sphincter muscle. Blocking this branch relaxes the sphincter and allows bladder emptying.

To achieve bladder voiding, the electrical conductor 24 is implanted in the subject with its stimulating end 28 positioned proximate or in contact with the pudendal nerve. The pick-up end 26 of the electrical conductor 24 extends into subcutaneous tissue located below the surface cathodic electrode 20. The surface cathodic and anodic electrodes 20, 22 are positioned preferably on the subject's skin above the hips. Since the pudendal nerve is present on both the left and right sides of the body, two electrical conductors 24 can optionally be positioned on both sides to achieve blocking. This would necessitate one surface anodic electrode 20, and either one or two surface cathodic electrodes 22. The electrical conductor 24 provides a conductive pathway for at least a portion of the electrical current flowing between the surface cathodic and anodic electrodes 20, 22 in the form of high frequency waveforms and transmits that portion of the electrical current to the pudendal nerve. Blocking of the pudendal nerve by stimulation with high frequency electrical pulses subsequently causes the urethral sphincter to open (as observed by a sudden large drop in intraurethral pressure), allowing bladder voiding. The pudendal nerve is blocked to allow bladder voiding until the bladder is empty.

The invention can also be used to alleviate pain, which generally refers to a localized sensation of discomfort resulting from the stimulation of specialized nerve endings. Peripheral nerves are nerves and ganglia outside the brain and spinal cord. In a mixed peripheral nerve, the thinnest exteroceptive sensory fibers convey impulses which are interpreted in sensation as pain. The present invention can thus be used to block sensory axons in peripheral nerves to reduce pain. For example, trigeminal neuralgia is a repeated and incapacitating pain affecting the lower portion of the face and arising from malfunction of the trigeminal nerve, which carries sensory information from the face to the brain and controls the muscles involved in chewing. The electrical conductor 24 is implanted having its pick-up end 26 proximate or in contact with a cranial nerve (such as the trigeminal nerve) and its stimulating end 28 positioned subcutaneously within the head. Surface cathodic and anodic electrodes 20, 22 are positioned on the skin of the head. The electrical conductor 24 provides a conductive pathway for at least a portion of the electrical current flowing between the surface cathodic and anodic electrodes 20, 22 in the form of high frequency cyclical waveforms transmits that portion of the electrical current to the trigeminal nerve. Blocking of the trigeminal nerve may subsequently reduce pain in patients with trigeminal neuralgia.

Spasticity, tremor and/or muscle weakness is an example of a further disorder to which the invention is applicable for blocking of neural impulses. Spasticity is characterized by a state of hypertonicity (i.e., an excessive tone of skeletal muscle with heightened deep tendon reflexes), and can cause muscle stiffness and awkward movements. It can occur as a result of stroke, cerebral palsy, multiple sclerosis or spinal cord injury. Nerve fibers involved with spasticity include sensory and motor nerves. The present invention can be used to block sensory and motor nerves to block muscle spasms. Referring again to FIG. 3, the median nerve 46 can be blocked (rather than activated as previously described) to alleviate flexure spasms occurring due to a stroke or multiple sclerosis. A flow of electrical current from the power source 40 is supplied in the form of high frequency cyclical waveforms via cathodic wire 42 into the skin 10 at the surface cathodic electrode 20 and the surface anodic electrode 22 via anodic wire 44. The electrical current flows through the termination 30, the pick-up end 26, the electrical conductor 24, the stimulating end 28, a portion of the median nerve 46, the tissue between stimulating end 28 and surface anodic electrode 22 including the skin underlying electrode 22, the surface anodic electrode 22, anodic wire 44 and the power source 40, thus completing the electrical circuit. Some of the current flowing between the stimulating end 28 and the surface anodic electrode 22 passes through the target body tissue (in this example, median nerve 46), thereby blocking nerve impulses along the median nerve 46 and preventing contraction of the muscle 16 of the arm 48.

The invention can also be used to reduce pain and spasticity by blocking the spinal cord. As an example, back pain or leg muscle spasms may be alleviated by blocking spinal nerves in the lumbar spine. The lumbar spinal nerves (L1 to L5) supply the lower parts of the abdomen and the back, the buttocks, some parts of the external genital organs, and parts of the legs. The electrical conductor 24 is implanted with its stimulating end 28 positioned between lumbar vertebrae into the lumbar spinal canal. The stimulating end 28 is placed proximate to the epidural space between the dura mater and the walls of the spinal canal. The pick-up end 26 is positioned subcutaneously in the lower back of the body. Surface cathodic and anodic electrodes 20, 22 are positioned on the skin of the lower back. The electrical conductor 24 provides a conductive pathway for at least a portion of the electrical current flowing between the surface cathodic and anodic electrodes 20, 22 in the form of high frequency cyclical waveforms and transmits that portion of the electrical current to the spinal cord. Blocking of the lumbar spinal nerves may subsequently reduce pain or spasticity in affected regions of the lower body.

The invention can be used to treat pathological tremor, Parkinson's disease, dystonia and other disorders by blocking deep brain nuclei. Such target tissues can include the basal ganglia which includes the subthalamic nucleus and substantia nigra. Parkinson's disease is a disorder of the basal ganglia. The electrical conductor 24 is implanted with its stimulating end 28 positioned proximate or in contact with the basal ganglia. The pick-up end 26 is positioned subcutaneously within the head. Surface cathodic and anodic electrodes 20, 22 are positioned on the skin of the head. The electrical conductor 24 provides a conductive pathway for at least a portion of the electrical current flowing between the surface cathodic and anodic electrodes 20, 22 in the form of high frequency waveforms and transmits that portion of the electrical current to the basal ganglia. The electrical current blocks the electrical signals that cause symptoms of movement disorders. The present invention may thus be useful in blocking the basal ganglia or other target deep brain nuclei to treat disorders in which movement is impaired.

When a Markush group or other grouping is used herein, all individual members of the group and all combinations and possible subcombinations of the group are intended to be individually included in the disclosure. Every formulation or combination of components described or exemplified herein can be used to practice the invention, unless otherwise stated. One of ordinary skill in the art will appreciate that methods, device elements, and materials other than those specifically exemplified can be employed in the practice of the invention without resort to undue experimentation. All art-known functional equivalents, of any such methods, device elements, and materials are intended to be included in this invention. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this invention. The invention illustratively described herein suitably may be practiced in the absence of any element or elements, limitation or limitations which is not specifically disclosed herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, can be exchanged with "consisting essentially of" or "consisting of".

Although the description herein contains many specificities, these should not be construed as limiting the scope of the invention, but as merely providing illustrations of some of the embodiments of the invention. Each reference cited herein is hereby incorporated by reference in its entirety. However, if any inconsistency arises between a cited reference and the present disclosure, the present disclosure takes precedence. Some references provided herein are incorporated by reference herein to provide details concerning the state of the art prior to the filing of this application, other references may be cited to provide additional or alternative device elements, additional or alternative materials, additional or alternative methods of analysis or application of the invention.

The invention is further illustrated in the following non-limiting Examples.

THE EXAMPLES

Example 1

Two experiments were performed on anesthetized cats using the present invention to achieve high-frequency blockade of the pudendal nerve.

Methods

Surgical procedures: Cats were pre-operatively medicated with acepromazine (0.25 mg/kg intramuscular), glycopyrrolate (0.01 mg/kg intramuscular) and buprenorphine (0.01 mg/kg intramuscular) and anesthetized with a mixture of isoflurane (2-3% in carbogen, flow rate 2 L/min). The trachea was cannulated and connected to a closed loop anesthetic system that monitored respiration rate and assisted ventilation. One jugular or cephalic vein was catheterized to allow administration of fluids and drugs. The bladder was exposed via a midline abdominal incision and catheterized to allow the addition and withdrawal of fluids and the measurement of pressure within the bladder with a pressure transducer (see below). A second catheter (Kendall, closed end Tom Cat catheter) was inserted into the urethra and connected to a second pressure transducer to allow measurement of intraurethral pressure. The pudendal nerves were exposed by incisions lateral to the base of the tail. Cuff or hook electrodes were placed on the pudendal nerve or its branches. At the end of the experiment, the animals were euthanized with Euthanyl™.

Pressure measurements: Bladder pressure and urethral pressure were monitored in most stimulation trials. The urethral catheter was attached to a Harvard Apparatus Pump 22 syringe pump and set to infuse saline at 0.2 mL/min to allow measurement of intraurethral pressure as per the method of Brown and Wickham. Both the bladder and urethral catheters were connected via Luer ports to Neurolog NL108D4/10 domes and NL108T4 isolated pressure transducers. The pressure signals were low-pass filtered at 30 Hz and sampled at a rate of 100 samples per second using a CED 1401 laboratory computer interface and sampling software.

Stimulators: Neurolog (Digitimer Ltd., Welwyn Garden City, UK) modules NL304 (period generator), NL403 (delay-width), NL510 (pulse buffer) and NL800 (stimulus isolator) were used to deliver constant current monophasic pulses and Grass (Grass-Telefactor, West Warwick, R.I., USA) SD9 and S48 stimulators were used to deliver constant voltage monophasic pulses.

Means of delivering stimulation: Two types of stimulation were tested, namely direct stimulation, and stimulus routing using the present invention. In direct stimulation, a stimulating electrode was placed on the exposed pudendal nerve and connected via an insulated lead wire to the cathodal output of the Grass stimulator. A second (indifferent) electrode comprising an alligator clip attached to the incised skin near the exposed pudendal nerve was connected to the anodal output of the Grass stimulator. In stimulus routing using the present invention, an implanted electrode comprising a pick-up end in the form of a metal disk or coiled wire connected via an insulated lead wire to a stimulating end was implanted so that the pick-up end was located subcutaneously over the lumbar spine under a surface cathodal electrode and the stimulating end was in contact with a pudendal nerve. The surface cathodal electrode was a conductive gel electrode (Kendall, H59P) applied to the shaved skin overlying the pick-up end and connected to the cathodal output of the Neurolog stimulator. A second surface electrode was placed a few centimeters rostral to the cathodal electrode and connected to the anodal output of the Neurolog stimulator.

Low frequency (20 Hz) direct stimulation via a hook electrode placed proximally on the pudendal nerve was used to elicit contractions of the external urethral sphincter. These contractions were monitored in terms of intraurethral pressure as increases in intraurethral pressure are indicative of contractions of the external urethral sphincter. During periods of low-frequency direct stimulation, bursts of high-frequency stimulation were delivered via the router system through a hook electrode placed more distally on the pudendal nerve. The efficacy of the router-mediated high-frequency stimulation in blocking the nerve activity evoked by the direct low frequency stimulation was thereby determined.

Results

Figure 5A:
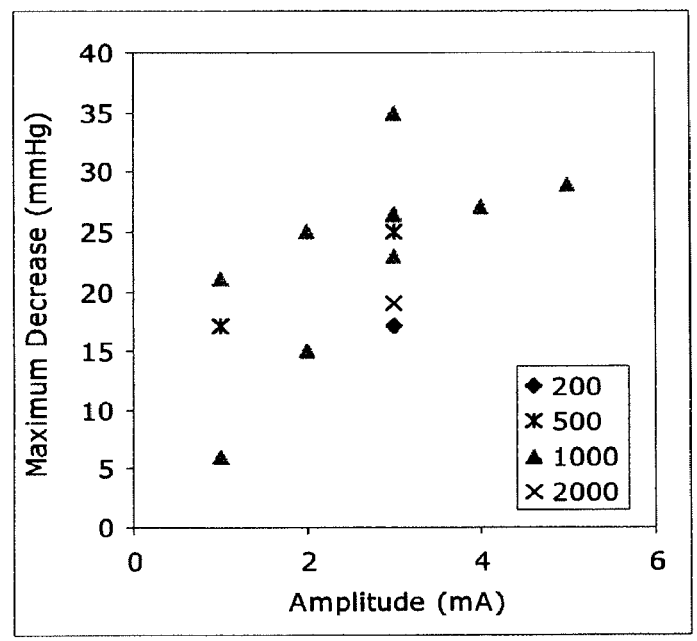
FIGS. 5A and 5B are graphs showing the effect of frequency and amplitude on pudendal nerve blocking.
Figure 5B:
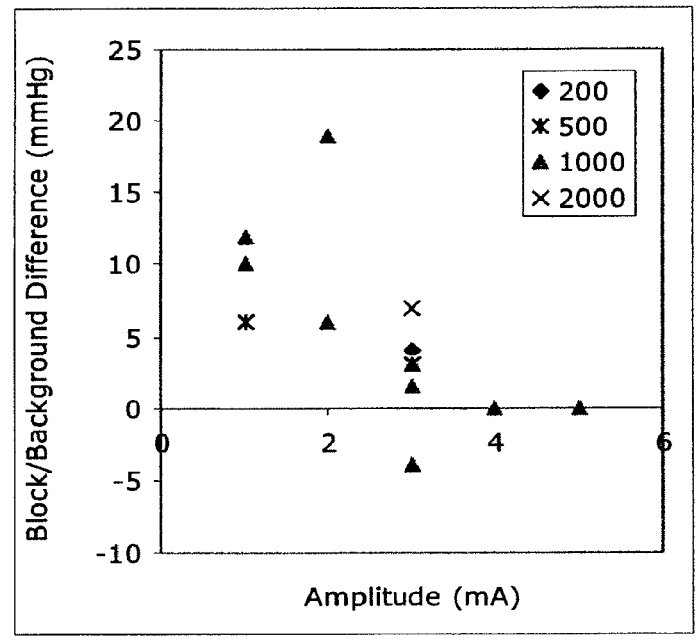

FIGS. 5A and 5B shows the results obtained in one animal when stimulation frequency and amplitude were varied and the efficacy of the pudendal nerve block was observed. The efficacy was measured by observing changes in the intraurethral pressure with the open port of the intraurethral catheter placed in the region of the external urethral sphincter. The right pudendal nerve was stimulated proximally at low frequency to elicit external urethral sphincter contractions while high frequency stimulation was applied distally to block the contractions. The maximum decrease in intraurethral pressure (FIG. 5A) was defined as the difference between the intraurethral pressure immediately before high frequency stimulation was applied and the minimal pressure obtained during high frequency stimulation. There appeared to be a trend towards larger decreases in intraurethral pressure at higher stimulation amplitudes. Blocking was obtained at all stimulation frequencies examined (i.e., 200, 500, 1000 and 2000 Hz).

FIG. 5B summarizes the effect of stimulation pulse frequency and amplitude on the ability of high frequency stimulation to return the intraurethral pressure to baseline. This provides a measure of the completeness of the block. The most complete blocking was achieved with stimulation amplitudes of 3 mA and higher. At a stimulation pulse amplitude of 3 mA, all tested frequencies (i.e., 200, 500, 1000 and 2000 Hz) elicited a nearly complete block. There was a general trend towards a more complete block at higher stimulation pulse amplitudes. A Y-axis value of zero indicates that the intraurethral pressure during high frequency stimulation was equal to the pre-stimulation baseline pressure.

Figure 6A:
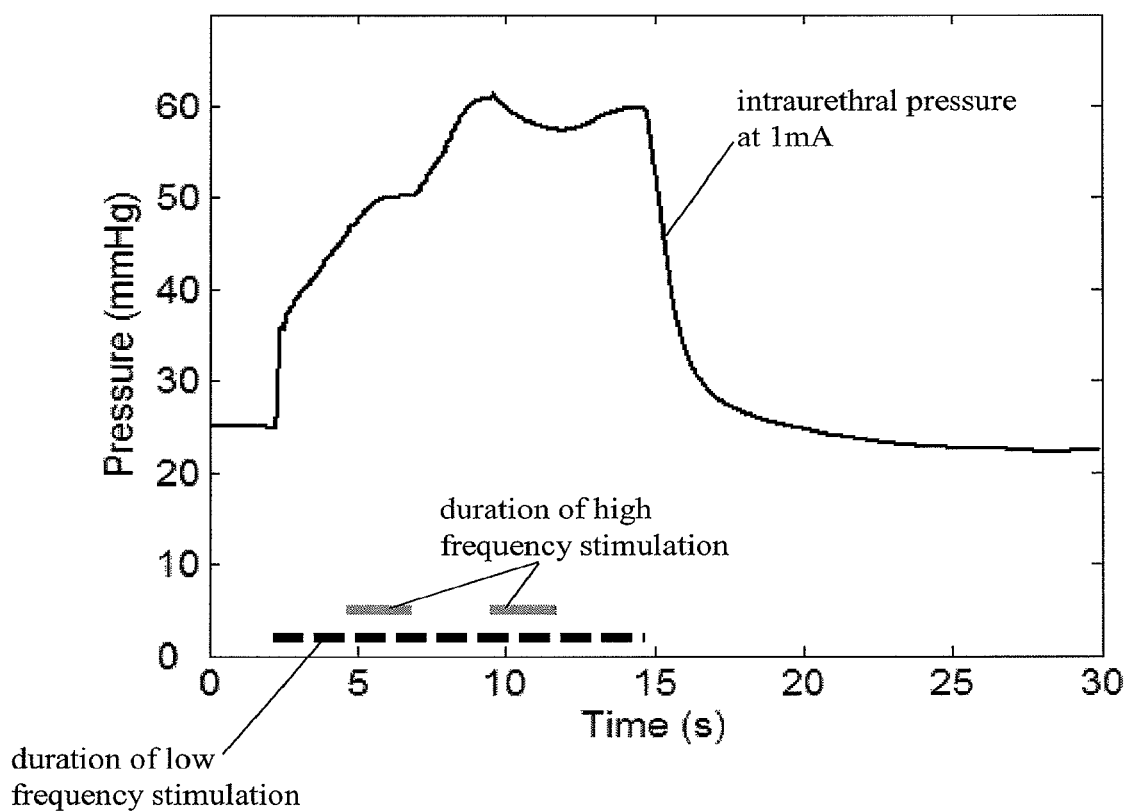
FIGS. 6A and 6B are graphs showing the effect of stimulation amplitudes of 1 mA (FIG. 6A) and 3 mA (FIG. 6B) with a frequency of 1 kHz on pudendal nerve blocking in one animal.
Figure 6B:
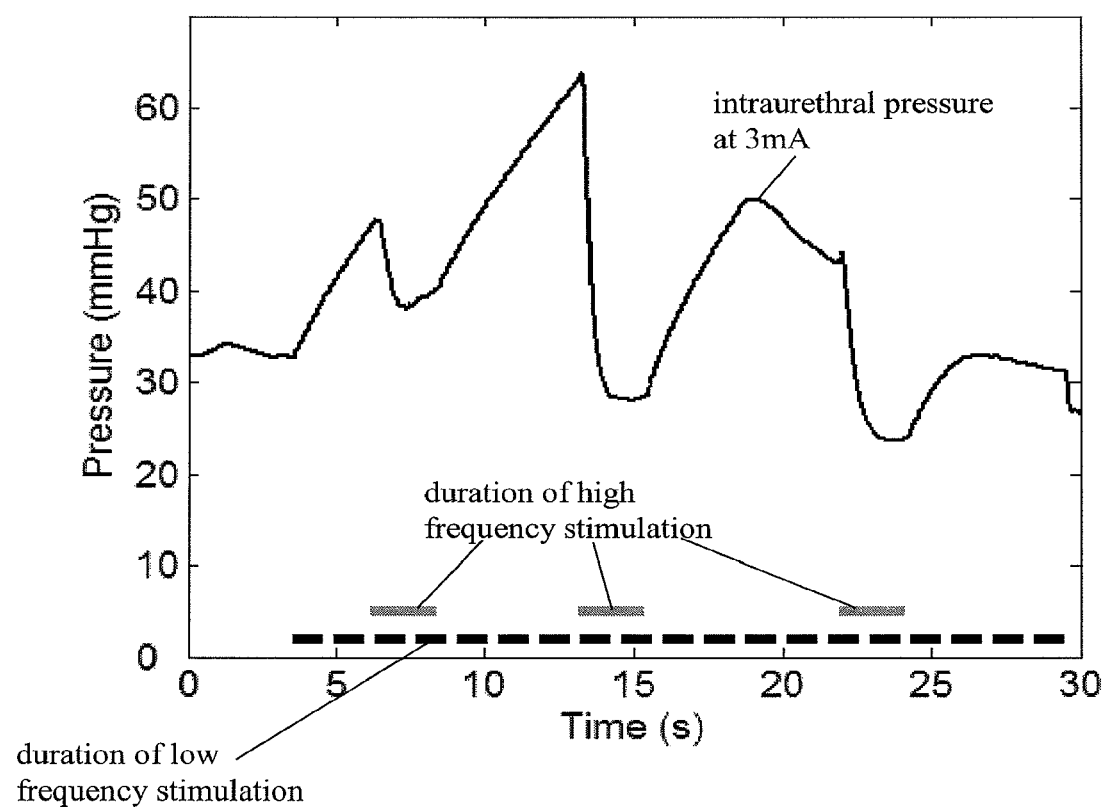

FIGS. 6A and 6B show the effect of stimulation pulse amplitude on pudendal nerve blocking in one animal. The traces represent intraurethral pressure obtained at 1 mA (FIG. 6A) and at 3 mA (FIG. 6B), the dashed bars indicate duration of low frequency stimulation and the solid bars indicate the duration of high frequency stimulation. Low frequency stimulation was applied proximally on the pudendal nerve with a monopolar hook electrode directly connected to the cathodal output of the Grass stimulus generator. High frequency stimulation was applied distally on the pudendal nerve with a monopolar hook electrode connected to the Neurolog stimulus generator via the stimulus routing system of the present invention. The anodal indifferent surface electrode was placed a few centimeters rostral to the cathodal surface electrode. Low frequency stimulation was delivered at a frequency of 20 Hz with pulses having an amplitude of 520 µA and a pulse width of 300 µs. High frequency stimulation was delivered at a frequency of 1 kHz with pulses having a pulse width of 100 µs. Stimulation with 1 mA pulse amplitudes had very little effect on the intraurethral pressure and elicited very little block of sphincter activity. However, with the stimulation pulse amplitude increased to 3 mA, a complete temporary and reversible block of sphincter activity was achieved.

Figure 7A:
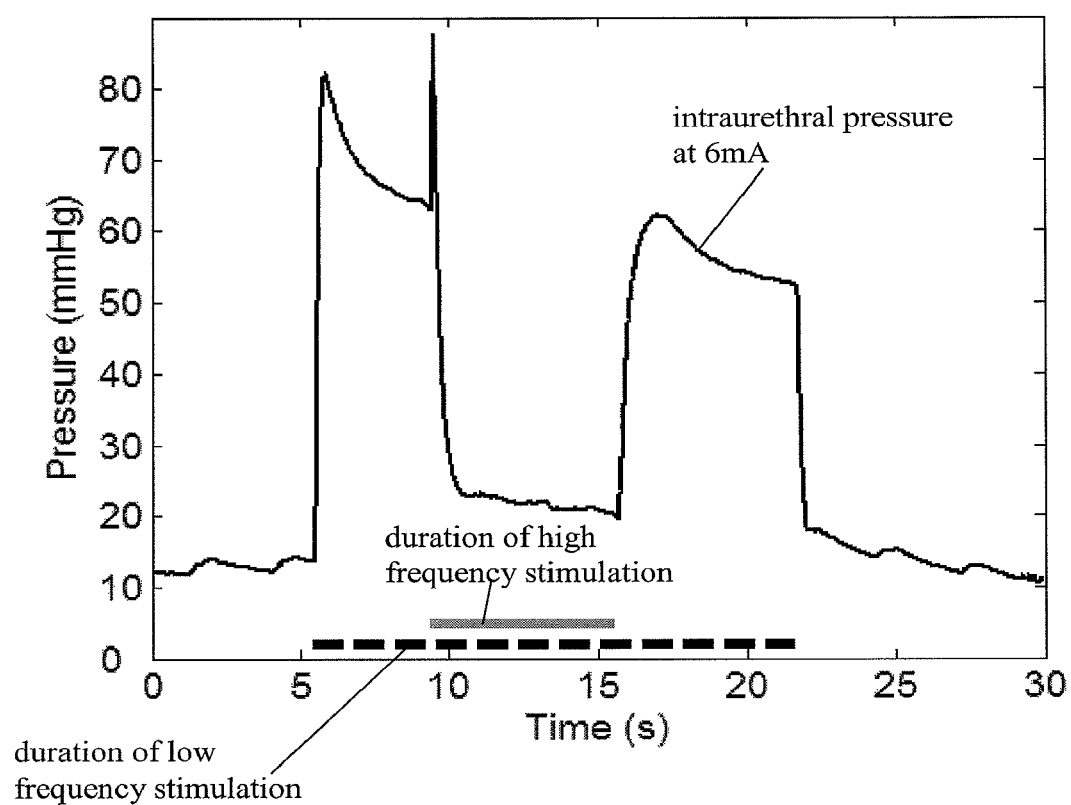
FIGS. 7A and 7B are graphs showing the effect of stimulation amplitudes of 6 mA (FIG. 7A) and 3 mA (FIG. 7B) with a frequency of 2 kHz on pudendal nerve blocking in one animal.
Figure 7B:
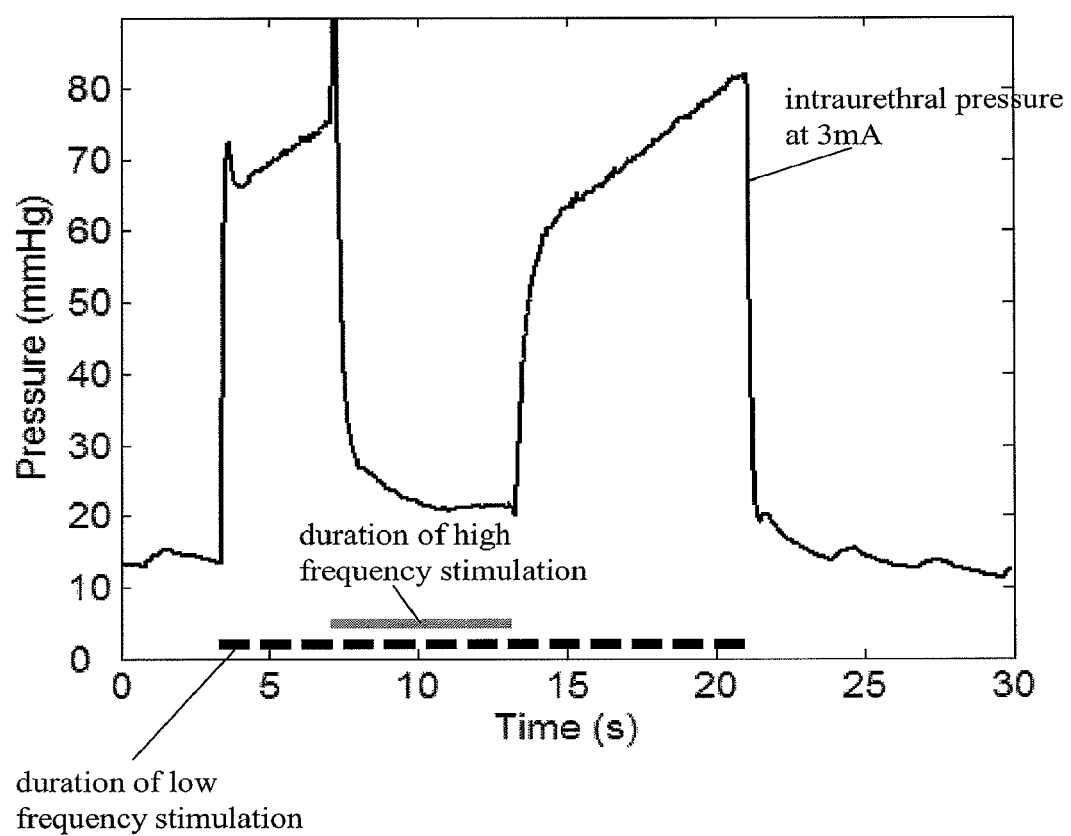

In the trials shown in FIGS. 7A and 7B, the stimulation frequency was 2 kHz. At 6 mA pulse amplitudes (FIG. 7A), a nearly complete block was achieved, but contractions of the leg under the surface cathodal electrode accompanied the stimulation. These contractions were maintained for the duration of the stimulation. At pulse amplitudes of 3 mA, similar blocking efficacy was achieved without concomitant leg contractions (FIG. 7B). In this trial, low frequency stimulation (duration indicated by dashed bars) was delivered at a frequency of 20 Hz with pulses having an amplitude of 300 µA and a pulse width of 200 µs, while high frequency stimulation (duration indicated by solid bars) was delivered at a frequency of 2 kHz with pulses having a pulse width of 150 µs.

Figure 8:
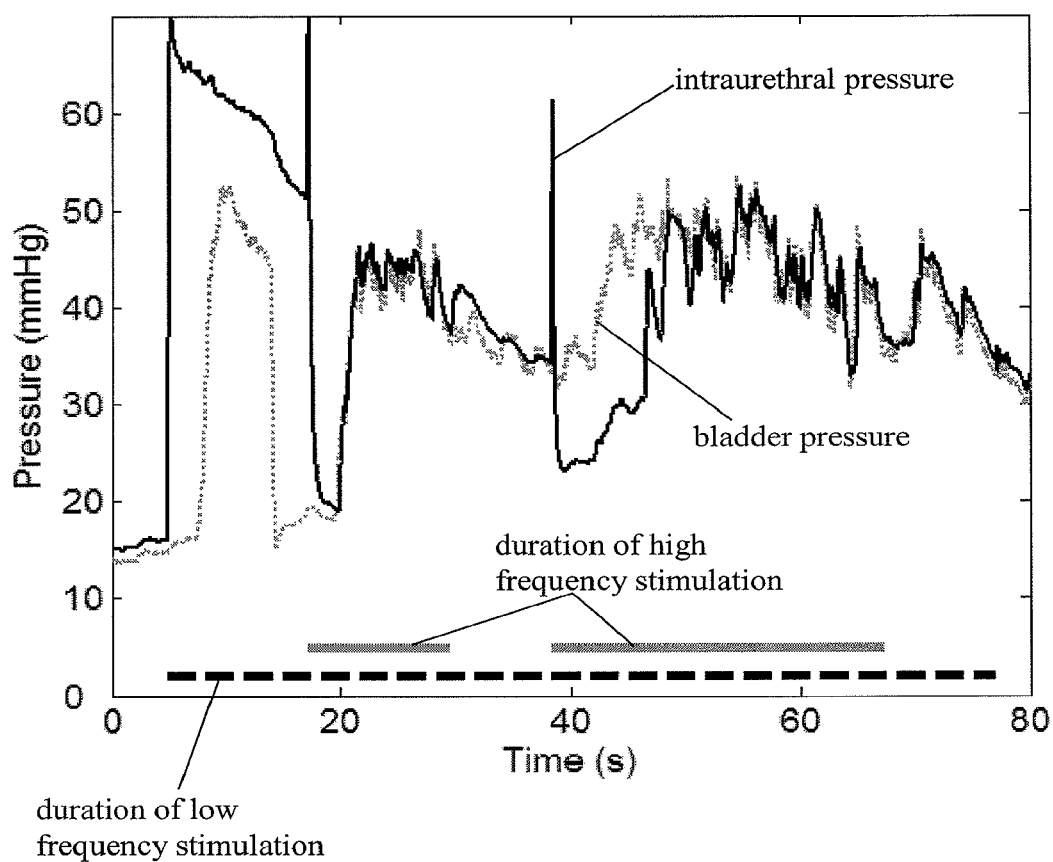
FIG. 8 is a graph showing the relationship between urethral pressure and bladder pressure during pudendal nerve blocking in one animal.

In further trials, in addition to low frequency stimulation of the proximal pudendal nerve and high frequency stimulation of the distal pudendal nerve, increases in bladder pressure were generated by manually applied abdominal pressure. FIG. 8 shows an example where this combined procedure was performed. FIG. 8 shows the effect of pudendal nerve blocking on intraurethral pressure in one animal. The solid trace is intraurethral pressure, the dotted trace is bladder pressure, the dashed bar indicates duration of low frequency stimulation and the solid bars indicate duration of high frequency stimulation. Low frequency stimulation was delivered at a frequency of 20 Hz with pulses having an amplitude of 330 µA and a pulse width of 200 µs. High frequency stimulation was delivered at a frequency of 2 kHz with pulses having an amplitude of 4 mA and a pulse width of 100 µs. Initial low frequency stimulation was used to generate an external urethral sphincter contraction after which the bladder pressure was increased by manual application of pressure to the abdomen. No voiding occurred during the first 20 seconds as intraurethral pressure was maintained higher than the manually generated bladder pressure by the direct pudendal nerve stimulation. Once high frequency stimulation of the distal pudendal nerve was applied, intraurethral pressure became equal to bladder pressure, indicating that the external sphincter was relaxed, and voiding occurred.

Several trials were performed in which the intraurethral catheter was removed to examine voiding. Complete voiding was achieved when high frequency stimulation was used to block low frequency stimulation-induced external urethral sphincter contractions and the bladder pressure was increased manually. In general, the results above suggest that use of the present invention and stimulation with an amplitude greater than 3 mA and a frequency greater than 200 Hz contributes to blocking transmission of activity in the pudendal nerve. Determination of stimulation parameters to produce an optimal block is under investigation. It will be understood by those skilled in the art that other stimulation parameters may produce better blocking results, particularly in other parts of the peripheral and central nervous systems. It will also be understood that it will be desirable to determine the stimulation parameters required to produce optimal nerve blocking on an individual basis, as these parameters may vary from subject to subject, depending upon the characteristics of the skin as well as the precise positioning of the components of the present invention.

D. Advantages of the Router System

As described above, the invention thus provides several advantages, primarily the capability of stimulating a target body tissue to either activate or block neural impulses depending upon the frequency and the disorder to be treated. Further, the present invention includes a means of "remote" stimulation, that is the surface cathodic and anodic electrodes 20, 22 do not have to be positioned over target body tissues. Remote target body tissues, such as nerves 12, can be stimulated to activate or block neural impulses from closely spaced surface cathodic and anodic electrodes 20, 22, by routing current through separate electrical conductors 24 simultaneously to several remote target body tissues.

Further, greater selectivity is provided in stimulating target body tissues to activate or block neural impulses. The electrical conductor 24 extends to a specific target body tissue, or multiple electrical conductors 24 can extend to multiple target body tissues. Stimulation is thus specific to the target body tissues, and stimulation of non-target body tissues is avoided. As an electrical conductor 24 of sufficient length is used to reach target body tissues, stimulation of target body tissues which are positioned deep within the body or organs such as the muscles, brain, cochlea, optic nerve, heart, bladder, urethra, kidneys and bones, can be achieved.

Stimulation to activate or block neural impulses is reproducible at will. The electrical conductor 24 is passive and can remain permanently implanted with the pick-up end 26 under the skin 10 beneath the site at which the surface cathodic electrode 20 would be placed, and the stimulating end 28 positioned proximate to the target body tissue. To the inventor's knowledge, difficulty has been encountered in positioning surface electrodes accurately to obtain acceptable selectivity of stimulation of body tissues. The inventor has discovered that surprisingly, the invention requires far less accuracy in positioning of the surface cathodic and anodic electrodes 20, 22; consequently, stimulation of body tissues to activate or block neural impulses is more accurately reproducible.

Further, the invention avoids problems inherent in other forms of stimulation. The conductors (i.e., electrical conductor 24, electrical return conductor 34) do not emerge through the skin, thus reducing the risk of infection which may arise with percutaneous devices. There is no need to construct an implant housing its own stimulator, signal generator or power source, or to provide radio-frequency or other telemetric command signals through the skin.

It will be apparent to one skilled in the art that modifications may be made to the illustrated embodiment without departing from the spirit and scope of the invention as hereinafter defined in the claims.

REFERENCES

Abdel-Gawad, M., Boyer, S., Sawan, M. and Elhilali, M. M. (2001) Reduction of bladder outlet resistance by selective stimulation of the ventral sacral root using high frequency blockade: a chronic study in spinal cord transected dogs. Journal of Urology 166:728-733.

Apkarian, J. A. and Naumann, S. (1991) Stretch reflex inhibition using electrical stimulation in normal subjects and subjects with spasticity. Journal of Biomedical Engineering 13:67-72.

Ashkan, K., Wallace, B., Bell, B. A. and Benabid, A. L. (2004) Deep brain stimulation of the subthalamic nucleus in Parkinson's disease 1993-2003: where are we 10 years on? Br J Neurosurg 18: 19-34.

Benabid, A. L., Pollak, P., Louveau, A., Henry, S. and De Rougemont, J. (1987) Combined (thalamotomy and stimulation) stereotactic surgery of the VIM thalamic nucleus for bilateral Parkinson disease. *Applied Neurophysiology* 50:344-346.

Bhadra, N. and Kilgore, K. L. (2005 Aug. 25) High-frequency electrical conduction block of mammalian peripheral motor nerve. Muscle Nerve. (Epub ahead of print)

Brindley, G. S., Polkey, C. E. & Rushton, D. N. (1982) Sacral anterior root stimulators for bladder control in paraplegia. *Paraplegia* 20:365-381.

Broseta, J., Garcia-March, G., Sanchez-Ledesma, M. J., Barbera, J. and Gonzalez-Darder, J. (1987) High-frequency cervical spinal cord stimulation in spasticity and motor disorders. Acta Neurochir Suppl (Wien) 39:106-111.

Filali, M., Hutchison, W. D., Palter, V. N., Lozano, A. M. and Dostrovsky, J. O. (2004) Stimulation-induced inhibition of neuronal firing in human subthalamic nucleus. Exp Brain Res 156(3):274-81.

Grill, W. M., Jr. and Mortimer, J. T. (1996) Quantification of recruitment properties of multiple contact cuff electrodes. *IEEE Trans. Rehabil. Eng.* (4(2):49-62.

Groen, J. and Bosch, J. L. (2001) Neuromodulation techniques in the treatment of the overactive bladder. BJU Int 87(8):723-731.

Handa, Y., Yagi, R. and Hoshimiya, N. (1998) Application of functional electrical stimulation to the paralyzed extremities. Neurologia Medico-Chirurgica 38:784-788.

Haugland, M. & Sinkjaer, T. (1999) Interfacing the body's own sensing receptors into neural prosthesis devices. *Technology & Health Care* 7:393-399.

Horch, K. W. and Dhillon, G. S., ed. (2004) Neuroprosthetics. Theory and Practice. Vol. 2. World Scientific, New Jersey.

Kralj, A. R. & Bajd, T. (1989) Functional Electrical Stimulation: Standing and Walking after Spinal Cord Injury. CRC Press, Boca Raton, Fla.

Landau, B. and Levy, R. M. (1993) Neuromodulation techniques for medically refractory chronic pain. Annu Rev Med 44:279-287.

Peckham, P. H., Marsolais, E. B. and Mortimer, J. T. (1980) Restoration of key grip and release in the C6 tetraplegic patient through functional electrical stimulation. *J. Hand Surg.* 5:462-469.

Peckham, P. H., Keith, M. W., Kilgore, K. L., Grill, J. H., Wuolle, K. S., Thrope, G. B., Gorman, P., Hobby, J., Mulcahey, M. J., Carroll, S., Hentz, V. R. and Wiegner, A. Implantable Neuroprosthesis Research G (2001) Efficacy of an implanted neuroprosthesis for restoring hand grasp in tetraplegia: a multicenter study. Archives of Physical Medicine & Rehabilitation 82:1380-1388.

Prochazka, A., Gauthier, M., Wieler, M. and Kenwell, Z. (1997) The bionic glove: an electrical stimulator garment that provides controlled grasp and hand opening in quadriplegia. *Arch. Phys. Med. Rehabil.* 78:608-614.

Shaker, H. and Hassouna, M. M. (1999) Sacral root neuromodulation in the treatment of various voiding and storage problems. International Urogynecology Journal & Pelvic Floor Dysfunction 10:336-343.

Shaker, H. S., Tu, L. M., Robin, S., Arabi, K., Hassouna, M., Sawan, M. and Elhilali, M. M. (1998) Reduction of bladder outlet resistance by selective sacral root stimulation using high-frequency blockade in dogs: an acute study. J Urol 160(3 Pt 1):901-7.

Solomonow, M., Eldred, E., Lyman, J. and Foster, J. (1983) Control of muscle contractile force through indirect high-frequency stimulation. Am J Phys Med 62:71-82.

Strojnik, P., Acimovic, R., Vavken, E., Simic, V. and Stanic, U. (1987) Treatment of drop foot using an implantable peroneal underknee stimulator. Scandanavian J. of Rehabil. Med. 19:37-43.

Tai, C., Roppolo, J. R. and de Groat, W. C. (2004). Block of external urethral sphincter contraction by high frequency electrical stimulation of pudendal nerve. J Urol 172(5 Pt 1):2069-72.

Tai, C., Roppolo, J. R. and de Groat, W. C. (2005). Response of external urethral sphincter to high frequency biphasic electrical stimulation of pudendal nerve. J Urol 174(2): 782-6.

Vodovnik, L., Bowman, B. R. and Winchester, P. (1984) Effect of electrical stimulation on spasticity in hemiparetic patients. International Rehabilitation Medicine 6:153-156.

Vodovnik, L. (1981) Therapeutic effects of functional electrical stimulation of extremities. Medical and Biological Engineering & Computing 19:470-478.

Waltz, J. M. (1997) Spinal cord stimulation: a quarter century of development and investigation. A review of its development and effectiveness in 1,336 cases. Stereotactic & Functional Neurosurgery 69:288-299.

Yu, D. T., Chae, J., Walker, M. E. and Fang, Z. P. (2001) Percutaneous intramuscular neuromuscular electric stimulation for the treatment of shoulder subluxation and pain in patients with chronic hemiplegia: a pilot study. Arch Phys Med Rehabil 82:20-25.

Patent Documents

Nathan, R. H. Device for generating hand function. U.S. Pat. No. 5,330,516, issued Jul. 19, 1994.

Prochazka, A., Wieler, M., Kenwell, Z. R., Gauthier, M. J. A. (1996) Garment for applying controlled electrical stimulation to restore motor function. U.S. Pat. No. 5,562,707, issued Oct. 8, 1996.

Prochazka, A. Method and apparatus for controlling a device or process with vibrations generated by tooth clicks. International Patent Application Publication No. WO 2004/034937, published Oct. 16, 2003.

Prochazka, A. Method of routing electrical current to bodily tissues via implanted passive conductors. International Publication No. WO 2005/070494 A1, published Aug. 4, 2005.

Sawan, M. and Elhilali, M. M. Electronic stimulator implant for modulating and synchronizing bladder and sphincter function. U.S. Pat. No. 6,393,323, issued May 21, 2002.

All publications mentioned in this specification are indicative of the level of skill in the art to which this invention pertains. All publications are herein incorporated by reference to the same extent as if each individual publication was specifically and individually indicated to be incorporated by reference. Although the foregoing invention has been described in some detail by way of illustration and example, for purposes of clarity and understanding it will be understood that certain changes and modifications may be made without departing from the scope or spirit of the invention as defined by the following claims.

The invention claimed is:

1. A system for electrically stimulating a target body tissue in a subject, comprising:
a surface cathodic electrode and a surface anodic electrode configured to make electrical contact with the subject's skin and to transmit electrical current when positioned in a spaced relationship on the subject's skin;
a stimulator external to the subject's body, electrically connected to the surface cathodic electrode and the surface anodic electrode, the stimulator being configured to supply direct, pulsatile, or alternating current to the surface cathodic electrode and the surface anodic electrode at a frequency from 1 Hz to 30 kHz; and
an implant configured to pick up a portion of the electrical current flowing between the surface cathodic electrode and the surface anodic electrode and to transmit the portion of the electrical current to the target body tissue, the implant comprising a passive electrical conductor of sufficient length to extend, once implanted, from subcutaneous tissue located below the surface cathodic electrode to the target body tissue, the electrical conductor having a pick-up portion and a stimulating portion and being insulated between its pick-up portion and its stimulating portion, the pick-up portion forming an electrical termination having a sufficient surface area to allow a portion of the electrical current to flow through the conductor, in preference to flowing through body tissue between the surface cathodic and anodic electrodes, and the stimulating portion forming an electrical termination for delivering the portion of electrical current to the target body tissue.

2. The system of claim 1, further comprising an electrical return conductor of sufficient length to extend, once implanted, from the target body tissue to subcutaneous tissue located below the surface anodic electrode, the return conductor having a collecting portion and a returning portion and being insulated between its collecting portion and its returning portion, the collecting portion forming an electrical termination having a sufficient surface area to allow a portion of the current delivered to the target body tissue to return through the return conductor in preference to returning through body tissue, and the returning portion forming an electrical termination to return the electrical current to the surface anodic electrode via the subcutaneous tissue and skin underlying the surface anodic electrode.

3. The system of claim 2, wherein at least one of the conductor and the return conductor is formed from a metal wire, carbon fibers, a conductive rubber or other conductive polymer, or a conductive salt solution in rubber.

4. The system of claim 1, wherein the termination on at least one of the pick-up portion or the stimulating portion is an enlarged surface in the form of a coil, a spiral, a cuff, a rod, or a plate or sheet in the form of an oval or polygon.

5. The system of claim 1, wherein the surface cathodic and anodic electrodes each comprise a conductive plate or sheet, a conductive gel electrode, a conductive rubber or polymer electrode that may be partially coated with an electrode paste or gel, or a moistened absorbent pad electrode.

6. The system of claim 1, wherein the terminations of the pick-up and delivery portions are formed from uninsulated end portions of the conductor itself or from other conductive materials.

7. The system of claim 1, further comprising a coating on at least one of the terminations, the coating being a conductive or capacitive coating, an oxide layer, an anti-inflammatory agent, an antibacterial agent, an antibiotic, or a tissue ingrowth promoter.

8. The system of claim 1, wherein the stimulator is configured to supply electrical current in the form of a cyclical monophasic wave form or in the form of a cyclical biphasic waveform.

9. The system of claim 1, wherein:
the implant is one implant from a plurality of implants, each of the plurality of implants configured to electrically block target body tissue independently or in unison, each implant from the plurality of implants configured to be implanted entirely under the subject's skin and to be of a sufficient length to extend to a different target body tissue, and
the surface cathodic electrode is one surface cathodic electrode from a plurality of surface cathodic electrodes, at least the surface cathodic electrode and the surface anodic electrode configured to be positioned relative to the plurality of implants to block the different target body tissues independently or in unison.

10. The system of claim 1, wherein:
the implant is one implant from a plurality of implants, each of the plurality of implants configured to electrically activate target body tissue independently or in unison, each implant from the plurality of implants configured to be implanted entirely under the subject's skin and to be of a sufficient length to extend to a different target body tissue, and the surface cathodic electrode is one surface cathodic electrode from a plurality of surface cathodic electrodes, at least the surface cathodic electrode and the surface anodic electrode configured to be positioned relative to the plurality of implants to activate the different target body tissues independently or in unison.

11. A method comprising at least one of electrically blocking or electrically activating a target body tissue in a subject using the system of claim 1.

12. The system of claim 1, wherein the stimulator is configured to supply electrical current in the form of a cyclical waveform at a frequency in the range of from 100 Hz to 20 kHz for blocking the target body tissue.

13. The system of claim 1, wherein the stimulator is configured to supply electrical current in the form of a cyclical waveform at a frequency in the range of from 100 Hz to 10 kHz for blocking the target body tissue.

14. The system of claim 1, wherein the stimulator is configured to supply electrical current in the form of a cyclical waveform at a frequency in the range of from 200 Hz to 5 kHz for blocking the target body tissue.

15. The system of claim 1, wherein the stimulator is configured to supply electrical current in the form of a cyclical waveform at a frequency in the range of from 1 kHz to 30 kHz for blocking the target body tissue.

16. The system of claim 1, wherein the stimulator is configured to supply electrical current in the form of a cyclical waveform at a frequency in the range of from 1 kHz to 20 kHz for blocking the target body tissue.

17. The system of claim 1, wherein the stimulator is configured to supply electrical current in the form of a cyclical waveform at a frequency in the range of from 1 kHz to 10 kHz for blocking the target body tissue.

18. The system of claim 1, wherein the stimulator is configured to supply electrical current at a frequency in the range of from 1 Hz to 100 Hz for activating the target body tissue.

19. The system of claim 1, wherein the stimulator is configured to supply electrical current at a frequency in the range of from 1 Hz to 50 Hz for activating the target body tissue.

20. The system of claim 1, wherein the stimulator is configured to supply electrical current at a frequency in the range of from 1 Hz to 20 Hz for activating the target body tissue.

21. The system of claim 1, wherein the stimulator is configured to supply electrical current in the form of a cyclical waveform at a frequency in the range of from 100 Hz to 30 kHz for blocking the target body tissue.

22. The system of claim 21, wherein the stimulator is configured to supply electrical current in a cyclical waveform selected from alternating current, pulsatile, sinusoidal, triangular, rectangular and sawtooth waveforms.

23. A method of treating a disorder by electrically stimulating a target body tissue in a subject, comprising:
implanting an implant entirely under the subject's skin, the implant configured to act as a conductive pathway for at least a portion of an electrical current flowing between a surface cathodic electrode and a surface anodic electrode positioned in a spaced relationship on the subject's skin and to transmit the portion of the electrical current to the target body tissue, the implant comprising a passive electrical conductor of sufficient length to extend, once implanted, from subcutaneous tissue located below the surface cathodic electrode to the target body tissue, the electrical conductor having a pick-up portion and a stimulating portion and being insulated between its pick-up portion and its stimulating portion, the pick-up portion forming an electrical termination having a sufficient surface area to allow a portion of the electrical current to flow through the conductor, in preference to flowing through body tissue between the surface cathodic electrode and the surface anodic electrode, such that the target body tissue is stimulated, and the stimulating portion forming an electrical termination to deliver the portion of electrical current to the target body tissue, the implant being implanted such that the pick-up portion is positioned in subcutaneous tissue located below the surface cathodic electrode and the stimulating portion is positioned proximate to the target body tissue;
positioning the surface cathodic and anodic electrodes in a spaced relationship on the subject's skin to make electrical contact with the skin, the surface cathodic electrode being positioned over the pick-up portion of the electrical conductor such that the portion of the electrical current is transmitted through the conductor to the target body tissue, and such that the electrical current flows through the target body tissue and returns to the anodic surface electrode through body tissues or through an implanted electrical return conductor extending between the target body tissue and subcutaneous tissue located below the surface anodic electrode; and
applying electrical current in at least one of a direct, pulsatile, or alternating current to at least one of the surface cathodic electrode and the surface anodic electrode, the electrical current being supplied by a stimulator external to the subject's body and electrically connected to the surface cathodic and anodic electrodes, the electrical current being applied at a frequency within the range of from 1 Hz to 30 kHz for stimulating the target body tissue.

24. The method according to claim 23, further comprising implanting an electrical return conductor entirely under the subject's skin, the return conductor being of sufficient length to extend, once implanted, from the target tissue to subcutaneous tissue located below the surface anodic electrode, the return conductor having a collecting portion and a returning portion and being insulated between its collecting portion and its returning portion, the collecting portion forming an electrical termination having a sufficient surface area to allow a portion of the electrical current delivered to the target body tissue to return through the return conductor in preference to returning through body tissue, and the returning portion forming an electrical termination to return the electrical current to the surface anodic electrode via the subcutaneous tissue and skin underlying the surface anodic electrode.

25. The method of claim 23, wherein electrical current is supplied at a frequency in the range of from 100 Hz to 30 kHz for blocking the target body tissue.

26. The method of claim 25, wherein the disorder is one or more of urinary retention, incontinence, pain, an autonomic disorder, spasticity, tremor, muscle weakness, Parkinson's disease, and dystonia.

27. The method of claim 26, wherein the body tissue is selected from a neural tissue in the peripheral or central nervous system or a nerve.

28. The method of claim 27, wherein the electrical current is supplied at a frequency in the range of from 100 Hz to 20 kHz.

29. The method of claim 27, wherein the electrical current is supplied at a frequency in the range of from 100 Hz to 10 kHz.

30. The method of claim 27, wherein the electrical current is supplied at a frequency in the range of from 200 Hz to 5 kHz.

31. The method of claim 27, wherein the electrical current is supplied at a frequency in the range of from 1 kHz to 30 kHz.

32. The method of claim 27, wherein the electrical current is supplied at a frequency in the range of from 1 kHz to 20 kHz.

33. The method of claim 27, wherein the electrical current is supplied at a frequency in the range of from 1 kHz to 10 kHz.

34. The method of claim 27, wherein the stimulator is configured to supply electrical current in a cyclical monophasic waveform or in a cyclical biphasic waveform.

35. The method of claim 27, wherein the implant is one implant from a plurality of implants, each of the plurality of implants configured to be implanted entirely under the subject's skin and being of a sufficient length to extend to a different target body tissue, and the surface cathodic electrode is one of a plurality of surface cathodic electrodes, the plurality of implants, the plurality of surface cathodic electrodes and the surface anodic electrode being collectively configured to electrically block more than one target body tissue independently or in unison, further comprising:
  positioning the plurality of surface cathodic electrodes and the surface anodic electrode on the subject's skin relative to the plurality of implants implanted entirely beneath the subject's skin; and
  supplying the electrical current to block the more than one target body tissue independently or in unison.

36. The method of claim 23, wherein the electrical current is applied at a frequency in the range of from 1 Hz to 100 Hz for activating the target tissue.

37. The method of claim 36, wherein the body tissue is selected from a neural tissue in the peripheral or central nervous system or a nerve.

38. The method of claim 36, wherein the electrical current is applied at a frequency in the range of from 1 Hz to 50 Hz.

39. The method of claim 36, wherein the implant is one implant from a plurality of implants, each of the plurality of implants configured to be implanted entirely under the subject's skin and being of a sufficient length to extend to a different target body tissue, and the surface cathodic electrode is one of a plurality of surface cathodic electrodes, the plurality of implants, the plurality of surface cathodic electrodes and the surface anodic electrode being collectively configured to electrically activate more than one target body tissue independently or in unison, further comprising:
  positioning the plurality of surface cathodic electrodes and the surface anodic electrode on the subject's skin relative to the plurality of implants implanted entirely beneath the subject's skin; and
  supplying the electrical current to activate the more than one target body tissue independently or in unison.

* * * * *